(12) United States Patent
Kirby et al.

(10) Patent No.: US 9,398,889 B2
(45) Date of Patent: Jul. 26, 2016

(54) RADIOGRAPHIC PHANTOM APPARATUSES

(71) Applicant: The Regents of the University of California, Oakland, CA (US)

(72) Inventors: Neil Kirby, Mountain View, CA (US); Cynthia Chuang, Sunnyvale, CA (US); Jean Pouliot, Mill Valley, CA (US)

(73) Assignee: The Regents Of The University Of California, Oakland, CA (US)

( * ) Notice: Subject to any disclaimer, the term of this patent is extended or adjusted under 35 U.S.C. 154(b) by 141 days.

(21) Appl. No.: 14/076,747

(22) Filed: Nov. 11, 2013

(65) Prior Publication Data
US 2014/0294140 A1    Oct. 2, 2014

Related U.S. Application Data

(60) Provisional application No. 61/483,316, filed on May 12, 2011.

(51) Int. Cl.
*A61B 6/00* (2006.01)
*A61B 6/03* (2006.01)
*G09B 23/28* (2006.01)

(52) U.S. Cl.
CPC .............. *A61B 6/583* (2013.01); *A61B 6/032* (2013.01); *G09B 23/286* (2013.01); *A61B 6/5247* (2013.01)

(58) Field of Classification Search
CPC ...... A61B 6/032; A61B 6/583; A61B 6/5247; G09B 23/286; G01N 2223/612; G01N 2223/3035; G06T 11/005
See application file for complete search history.

(56) References Cited

U.S. PATENT DOCUMENTS

| | | | | |
|---|---|---|---|---|
| 2003/0086535 | A1* | 5/2003 | Teppaz | A61B 6/583 378/207 |
| 2006/0002519 | A1* | 1/2006 | Jenkins | A61N 5/1048 378/207 |
| 2008/0240364 | A1 | 10/2008 | Main et al. | |
| 2008/0298540 | A1* | 12/2008 | Serban | A61B 6/583 378/18 |
| 2009/0088620 | A1* | 4/2009 | Zagorchev | A61B 6/5247 600/407 |
| 2010/0047752 | A1* | 2/2010 | Chan | B29C 33/3857 434/272 |
| 2010/0167251 | A1* | 7/2010 | Boutchko | A61B 5/416 434/267 |
| 2010/0278409 | A1* | 11/2010 | Wiemker | A61B 6/583 382/131 |
| 2011/0251478 | A1* | 10/2011 | Wieczorek | A61B 5/1127 600/411 |
| 2013/0267829 | A1* | 10/2013 | Ojha | A61B 6/032 600/411 |

OTHER PUBLICATIONS

Kashani et al., Objective assessment of deformable image registration in radiotherapy, Dec. 2008, Med. Phys., vol. 35, No. 12, p. 5944, 5945, 5948.*

Lawson et al., Quantitative evaluation of a cone-beam computed tomography-planning computed tomography deformable image registration method for adaptive radiation therapy, Aug. 2007, Journal of Applied Clinical Medical Physics, vol. 8, No. 4, p. 98, 100, 111.*

(Continued)

*Primary Examiner* — Hoon Song
(74) *Attorney, Agent, or Firm* — Mintz Levin Cohn Ferris Glovsky and Popeo, P.C.

(57) ABSTRACT

There is provided a radiographic phantom for inter alia mimicking specific anatomical parts in a computerized tomography scan. Methods are provided for a variety of purposes including detecting a difference between a measured optical deformation of a radiographic phantom pair and a theoretical deformation of the radiographic phantom pair.

19 Claims, 20 Drawing Sheets

(56) References Cited

OTHER PUBLICATIONS

Miguel et al., Visualization and Tracking of an Inflatable Balloon Catheter Using SSFP in a Flow Phantom and in the Heart and Great Vessels of Patients, May 2004, Magnetic Resonance in Medicine, vol. 51, p. 989.*

Barron, J. L. et al. "Performance of Optical Flow Techniques" *International Journal of Computer Vision* 12.1 (1994): 43-77.

Horn, B. et al. "Determining Optical Flow" *Artificial Intelligence* 17.1-3 (1981): 185-203.

Lu, W. et al. "Fast free-form deformable registration via calculus of variations." Physics in Medicine and Biology 49(2004): 3067-3087.

Lucas, B. et al. "An iterative image registration technique with an application to stereo vision" *Proceedings of Imaging Understanding Workshop* (1981): 121-130.

Rogelj, P. et al. "Symmetric image registration" *Medical Image Analysis* 10 (2006): 484-493.

Thirion, J.-P. "Image matching as a diffusion process: an analogy with Maxwell's demons" *Medical Image Analysis* 2.3 (1998): 243-260.

Wang, He. et al. "Validation of an accelerated 'demons' algorithm for deformable image registration in radiation therapy" *Physics in Medicine and Biology* 50 (2005):2887-2905.

\* cited by examiner

Fig. 10A    Fig. 10B
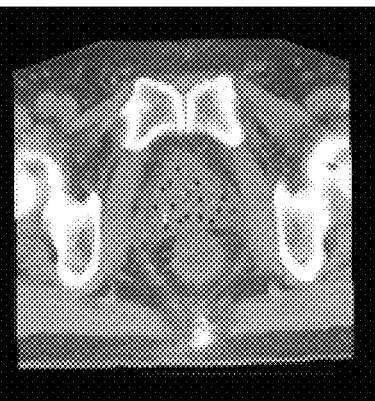
Fig. 10C
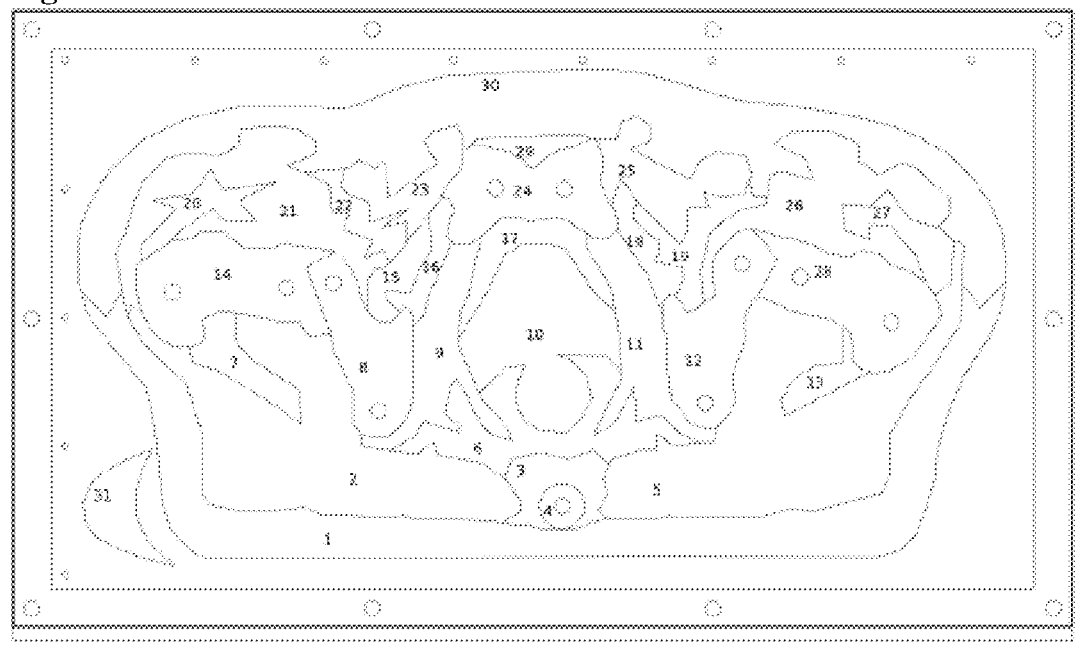

RADIOGRAPHIC PHANTOM APPARATUSES

CROSS-REFERENCES TO RELATED APPLICATIONS

This application is a continuation of International Application No. PCT/US2012/037802, filed May 14, 2012, which claims the benefit of U.S. Provisional Patent Application No. 61/485,316, filed May 12, 2011, the content of each of which is hereby incorporated herein by reference in its entirety and for all purposes.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Patient anatomy constantly changes and deforms throughout the course of a radiation treatment. This creates uncertainty in the delivered radiation dose and affects the treatment outcome. A substantial amount of research has been focused on developing deformation algorithms specifically for this issue. See e.g., Bajcsy, R. & Kovacic, S., 1989, Comput. Vis. Graph. Image Process. 46:1-21; Bookstein, F. L., 1989, IEEE Trans. Pattern Anal. Mach. Intell., 567-585; Davatzikos, C., et al., 1996, IEEE Trans. Med. Imaging 15:112-115; Meyer, C. R., et al., 1997, Med. Image Anal. 1:195-206; Thirion, J. P., 1998, Med. Image Anal. 2:243-260; D'Agostino, E., et al., 2003, Med. Image Anal. 7:565-575; Kybic, J. & Unser, M., 2003, IEEE Trans. Image Process. 12:1427-1442; Lu, W. G., et al., 2003, Phys. Med. Biol. 49:3067-3087; Coselmon, M. M., 2004, et al., Med. Phys. 31:2942-2948; Wang, H., et al., 2005, Phys. Med. Biol. 50:2887-2905; Brock, K. K., et al., 2005, Med. Phys. 32:1647-1659; Foskey, M., et al., 2005, Phys. Med. Biol. 50:5869-5892.

The resulting variety of these algorithms can produce distinctly different deformation predictions. Therefore, before the implementation of the deformation algorithms can reach its full potential, further work is needed to develop quality assurance techniques for verifying their accuracy. The radiographic phantom described herein addresses inter alia this effort.

Currently, there are methods to test the accuracy of deformation algorithms, but these methods have some shortcomings. These methods fall into three basic categories: contour comparison [Foskey, et al., 2005, Id.; Heath, E., et al., 2007, Med. Phys. 34:4409-4421; Serban, M., et al., 2008, Med. Phys. 35:1094-1102; Wijesooriya, K., et al., 2008, Med. Phys. 35, 1251-1260], landmark tracking [Meyer, C. R., et al., 1997, Id.; Heath, E., et al., 2007, Id.; Serban, M., et al., 2008, Id.; Kerdok, A. E., et al., 2001, "TruthCube: establishing physical standards for real time soft tissue simulation," Proceedings of the Int. Workshop on Deformable Modeling and Soft Tissue Simulation, Bonn, Germany; Lu, W. G., et al., 2004, Id.; Coselmon, M. M., et al., 2004, Id.; Wang, H., et al., 2005, Id.; Brock, K. K., et al., 2005, Id.; Rietzel, E. & Chen, G. T., 2006, Med. Phys. 33:4423-4430; Kashani, R., et al., 2007, Med. Phys. 34:2785-2788], and simulated deformations [D'Agostino, E., et al., 2003, Id.; Kybic, J. & Unser, M., 2003, Id.; Lu, W. G., et al., 2004, Id.; Wang, H., et al., 2005, Id.]

In the first of these methods, surface contours are created for a volume on images before and after deformation. Then, the initial contours are deformed, according to a deformation algorithm, and compared to those created on the distorted image. Without wishing to be bound by any theory, it is believed that the use of this method for a quantitative comparison is problematic. For example, since contour comparison occurs between surfaces, deformation errors that are tangential to the surfaces are not measured. In addition, contour comparison does not directly determine deformation accuracy for the points inside the surface.

For the second test category, visible landmarks are either identified on an existing image or they are created with the implantation of radiopaque markers. The locations of these landmarks are measured before and after the image deformation. Then, these measurements can be compared to the predictions of a deformation algorithm. Without wishing to be bound by any theory, it is believed that at least one problem with this method is that any prominent landmark will also stand out to the algorithm. Thus, these points might not be representative of the deformation errors for the volume as a whole. The images can be processed to remove the markers prior to their use by an algorithm; however, even the processing remnants could affect the deformation predictions.

For the third test category, deformations are applied digitally to an image. Then, the applied deformation is compared directly to the algorithm predictions. The deformation can be based on a physical model of the system, but this requires a firm biomechanical understanding of the local anatomy. See e.g., Brock, K. K., et al., 2005, Id.; Bharatha, A., et al., 2001, Med. Phys. 28:2551-2560; Brock, K. K., et al., 2002, Med. Phys. 29:1403-1405; Werner, R., et al., 2009, Med. Phys. 36:1500-1511; Almayah, A., et al., 2010a, Med. Phys. 37:4560-4571; Almayah, A., et al., 2010b, Phys. Med. Biol. 55:6491-6500. Without wishing to be bound by any theory, it is believed that at least one issue with this method is that the deformed image would have the same noise variations as the original image, which would affect the determined deformation. Additional noise could be created on the deformed image, but this would not represent the discrepancies of two distinct images.

By the present application there are provided methods and devices to overcome the mentioned shortcomings of the verification techniques currently available by, e.g., reducing the anatomy and its deformations to a two-dimensional system. This system is visible through a transparent, e.g., acrylic, plate, which allows the deformation markers to be non-radiopaque. Thus, these markers will not appear on the scanned images and do not perturb the deformation algorithms. The transparency of the surface markers permits them to be placed at a high density and, therefore, also allows for a measurement of the complete deformation field, rather than just the deformation of a few points. Predicted deformations for the scanned images of the device can be directly compared to these measured deformations.

A two-dimensional phantom can be tailor-made to represent the imaging and elastic properties of any anatomical site. For example, the deformations measured by the phantom can be applied to actual patient CT images to create deformed CT images. These simulated deformations would not require detailed computational modeling in the formulation of a deformable registration comparison.

BRIEF SUMMARY OF THE INVENTION

In a first aspect, there is provided a method of detecting a difference between a measured optical deformation of a radiographic phantom pair and a theoretical deformation of the radiographic phantom pair. The method includes (i) comparing a first optical image of a non-deformed radiographic phantom to a second optical image of a deformed radiographic phantom thereby obtaining a measured optical deformation. The method further includes (ii) performing a deformable registration method between a first computerized tomography (CT) image of the non-deformed radiographic phantom and a second CT image of the deformed radiographic phantom using a deformable registration algorithm thereby obtaining a theoretical deformation. The method further includes (iii) comparing the measured optical deformation with the theoretical deformation thereby determining a difference between the measured optical deformation and the theoretical deformation.

In another aspect, there is provided a radiographic phantom. The radiographic phantom includes: (i) two parallel plates; and (ii) a radiographic phantom material interposed between the parallel plates, wherein the radiographic phantom material includes a soft phantom material and a plurality of optically detectable non-radiopaque markers in spatial communication with the soft phantom material.

In another aspect, there is provided a computerized tomography apparatus. The computerized tomography apparatus includes: (i) a CT scanner including an X-ray source and an X-ray detector; and (ii) a radiographic phantom between the X-ray source and the X-ray detector. The radiographic phantom includes (a) two parallel plates; and (b) a radiographic phantom material interposed between the parallel plates, wherein the radiographic phantom material includes a soft phantom material and a plurality of optically detectable non-radiopaque markers in spatial communication with the soft phantom material.

In another aspect, there is provided a method for verifying a method for deformable registration. The method includes obtaining a first optical image and a first computerized tomography (CT) image of a non-deformed radiographic phantom. The method further includes obtaining a second optical image and a second CT image of a deformed radiographic phantom. The method further includes comparing the second optical image with the first optical image, thereby obtaining a measured optical deformation. The method further includes performing a deformable registration method between the second CT image and the first CT image, thereby obtaining a theoretical deformation. The method further includes comparing the measured optical deformations with the theoretical deformation, thereby verifying the method for deformable registration.

In another aspect, there is provided a method for identifying a method for deformable registration. The method includes obtaining a first optical image and a first CT image of a non-deformed radiographic phantom. The method further includes obtaining a second optical image and a second CT image of a deformed radiographic phantom. The method further includes comparing the second optical image to the first optical image, thereby obtaining a measured optical deformation. The method further includes performing a first method for deformable registration between the second CT image and the first CT image, thereby obtaining a first theoretical deformation. The method further includes comparing the measured optical deformation with the first theoretical deformation, thereby obtaining a first deformable registration error metric. The method further includes performing a second method for deformable registration between the second CT image and the first CT image, thereby obtaining a second theoretical deformation. The method further includes comparing the measured optical deformation with the second theoretical deformation, thereby obtaining a second deformable registration error metric. The method further includes comparing the first deformable registration error metric with the second deformable registration error metric, thereby identifying a method for deformable registration.

In another aspect, there is provided a method for testing for quality assurance of a method for deformable registration. The method includes obtaining a first optical image and a first CT image of a non-deformed radiographic phantom. The method further includes obtaining a second optical image and a second CT image of a deformed radiographic phantom. The method further includes comparing the second optical image to the first optical image, thereby obtaining a first measured optical deformation. The method further includes performing a method for deformable registration between the second CT image and the first CT image, thereby obtaining a first theoretical deformation. The method further includes comparing the first measured optical deformation with the first theoretical deformation, thereby obtaining a reference deformable registration error metric. The method further includes obtaining a third optical image and a third CT image of a non-deformed radiographic phantom under conditions where the third CT image may have changed relative to the first CT image. The method further includes obtaining a fourth optical image and a fourth CT image of a deformed radiographic phantom under conditions where the fourth CT image may have changed relative to the second CT image. The method further includes comparing the fourth optical image to the third optical image, thereby obtaining a second measured optical deformation. The method further includes performing the method for deformable registration between the fourth CT image and the third CT image, thereby obtaining a second theoretical deformation. The method further includes comparing the second measured optical deformation with the second theoretical deformation, thereby obtaining a test deformable registration error metric. The method further includes comparing the reference deformable registration error metric with the test deformable registration error metric, thereby testing for quality assurance of a method for deformable registration.

In another aspect, there is provided a method for improving a method for deformable registration. The method includes obtaining a first optical image and a first CT image of a non-deformed radiographic phantom. The method further includes obtaining a second optical image and a second CT image of a deformed radiographic phantom. The method further includes comparing the second optical image to the first optical image, thereby obtaining a measured optical deformation. The method further includes performing a method for deformable registration between the second CT image and the first CT image, thereby obtaining a theoretical deformation. The method further includes comparing the measured optical deformation with the theoretical deformation, thereby providing a deformable registration error metric. The method further includes identifying regions of error within the deformable registration error metric. The method further includes identifying components of the deformable registration algorithm corresponding to the regions of error within the deformable registration error metric, thereby improving the method for deformable registration.

In another aspect, there is provided a non-deformed radiographic phantom, which includes two parallel plates having radiographic phantom material interposed therebetween. The radiographic phantom material includes bony phantom material, soft phantom material; and surface markers attached to the soft phantom material.

In another aspect, there is provided a deformed radiographic phantom, which includes two parallel plates having radiographic phantom material interposed therebetween. The radiographic phantom material includes bony phantom material, soft phantom material, and surface markers attached to the soft phantom material.

BRIEF DESCRIPTION OF THE DRAWINGS

FIG. 2C depicts the determined deformation field, where the locations of the before and after markers appear as points, and the deformation is indicated by arrows.

FIG. 4A depicts the similarity metrics CC and SSD, which produced virtually identical results for this comparison. FIG. 4B depicts the MI similarity metric. FIG. 4C depicts the SAD similarity metric.

FIG. 9A depicts a typical CT image taken of a radiographic phantom having a radiographic encasement. FIG. 9B depicts a typical CT image taken of a radiographic phantom which lacks a radiographic encasement.

FIGS. 10A-10D. FIG. 10A depicts a CT scan image of a subject showing a region about the bladder. FIG. 10B depicts a follow-up CT scan image wherein the bladder holds less fluid. FIG. 10C depicts the area of FIGS. 10A-10B divided into a set of geometric shapes. The numbering of components within FIG. 10C is arbitrary. FIG. 10D depicts a CT scan image of the phantom for comparison with FIG. 10B.

FIG. 11A depicts an acrylic sheet during the cutting process. FIGS. 11B-11D depict the construction of two-part molds for each cut piece.

FIG. 17A depicts the machining of the phantom cover. FIG. 17B depicts the placement and drilling of the mounting holes.

FIG. 20A depicts the accuracy of techniques of deformation registration with respect to rigid registration. The ordinate is the fraction ($10^0$=100%) of markers with a distance to agreement larger than a given error as a function of error. Legend of methods: 1: Lucas-Kanade; 2: Original Horn and Schunck; 3: Inverse consistency Horn and Schunck (HS); 4: iterative optical flow; 5: fast iterative optical flow; 6: symmetric force demons; 7: fast demons; 8: fast demons with elastic regularization; 9: fast form via calculus of variations (COV); 10: MIMvista™ software; 11: Velocity Medical Solutions (B-spline deformation); 12: rigid. FIG. 20B depicts the algorithm accuracy versus RMS difference. See Example 3. Legend of methods: same as FIG. 20A.

DETAILED DESCRIPTION OF THE INVENTION

I. Definitions

Figure 1:
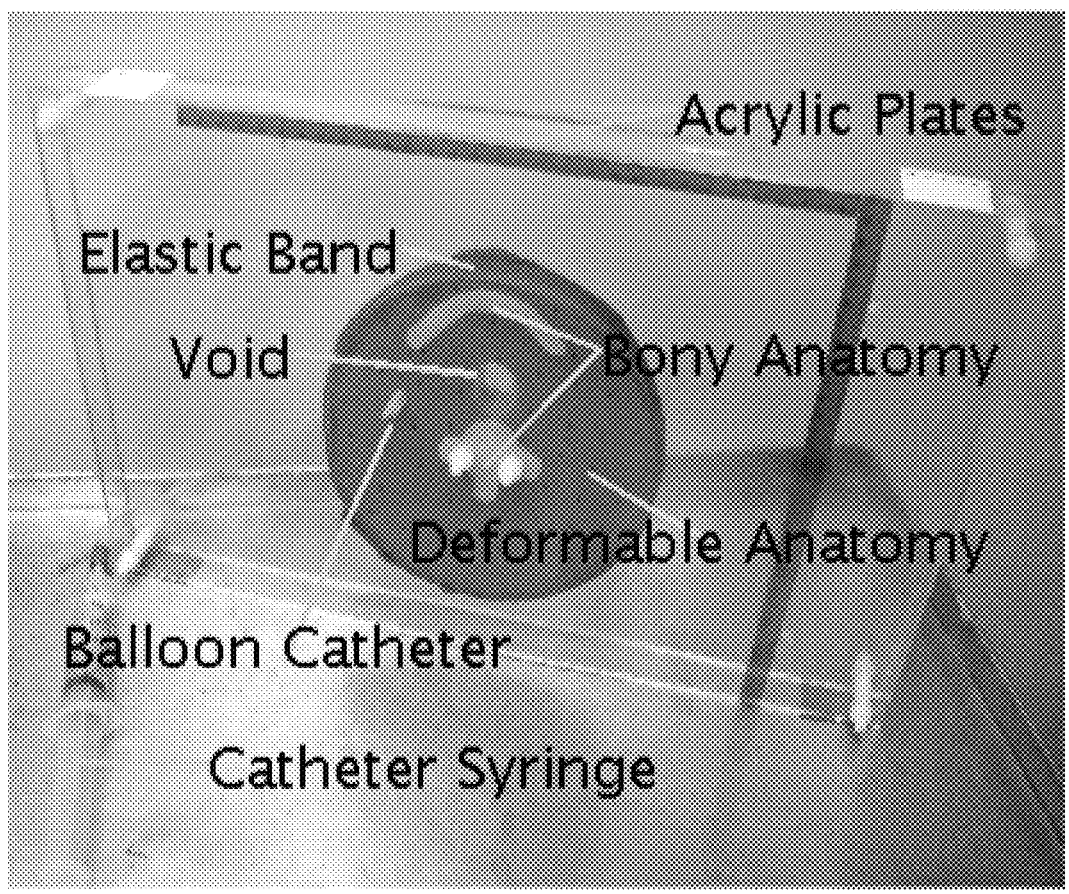
FIG. 1 depicts an assembled prototype of a two-dimensional deformable phantom described herein.

An "optical image" as used herein means a digital image obtained using an optical detection device such as a digital camera.

A "computerized tomography (CT) image" as used herein means a digital image obtained using X-ray computed tomography (also referred to as Computed tomography (CT scan) or Computed axial tomography (CAT scan)).

The term "radiographic phantom" (also referred to herein as a "phantom") refers to an apparatus having optically detectable non-radiopaque markers, wherein the apparatus is designed such that its computerized tomography (CT) image mimics a CT image of a plane of at least a portion of a mammalian anatomy (e.g. human anatomy). The plane may be, for example, an axial plane, sagittal plane, coronal plane or a transversal plane.

The terms "radiographic phantom-pair," "phantom-pair" and the like refer to two radiographic phantoms which differ in a substantial way, e.g. by the incorporation of a deformation element in the phantom material of one member of the phantom-pair. The term "deformation element" refers to a physical feature included within a radiographic phantom which serves to differentiate a non-deformed radiographic phantom from a deformed radiographic phantom. A deformation element may serve to differentiate between the members of a radiographic phantom-pair based at least in part on the shape, position or size of the deformation element in one member of the radiographic pair relative to the other member of the radiographic pair. The deformation element in one member of the radiographic phantom-pair may change the shape and position of surrounding radiographic material within the radiographic phantom in one member of the radiographic phantom-pair relative to the other member of the radiographic phantom-pair. Exemplary deformation elements may include, for example, the expanded tip of a balloon catheter or an additional material inserted into the radiographic phantom (e.g., a piece of non-radiographic plastic). In one embodiment, both radiographic phantoms of a radiographic phantom-pair independently incorporate different deformation elements (e.g. of different size, shape or position). For example, the deformation element incorporated into one member of a radiographic phantom-pair is deformed to a different degree or amount relative to the deformation element incorporated into the other member of radiographic phantom-pair. In other embodiments, only one member of a radiographic phantom-pair incorporates a deformation element.

A "non-deformed radiographic phantom" as used herein refers to one radiographic phantom of a radiographic phantom-pair wherein the other radiographic phantom of the radiographic phantom-pair is referred to herein as a "deformed radiographic phantom." Typical deformations include, e.g., mimicking the reduction in the size of tumor during therapy and the corresponding changes in the position and size of adjacent tissue. The term "deformed radiographic phantom" refers to a radiographic phantom in which some feature (e.g., size, displacement and the like) or plurality of features of the bony phantom material and/or the soft phantom material have been deformed relative to the non-deformed radiographic phantom. Deformation can be realized by a variety of methods. For example, a catheter balloon tip disposed within the soft phantom material can be inflated or deflated, thus providing a deformation. The deformation can result in, e.g., displacement of adjacent soft phantom material and/or displacement of adjacent bony phantom material. In another example, an insert (i.e., deformation element) such as an acrylic insert or non-radiopaque material insert, can be inserted into the soft phantom material to mimic the position and size of a physiological object, e.g., a tumor, within the phantom material of the deformed radiographic phantom, relative to the non-deformed radiographic phantom. The non-deformed radiographic phantom may contain no deformation element or a different deformation element (e.g. different size, shape or position).

Unless indicated otherwise, the terms "deform," "deformed," "deformation," and the like are used herein as relative terms. Therefore, in some embodiments, the non-deformed radiographic phantom does not contain a deformation element and the deformed radiographic phantom includes a deformation element. In one embodiment, the deformed radiographic phantom does not contain a deformation element and the non-deformed radiographic phantom includes a deformation element. In one embodiment the non-deformed radiographic phantom and the deformed radiographic phantom include deformation elements of substantially different size, shape and/or composition.

A "deformable registration method" is a method in which a first CT image (commonly referred to as a "fixed" CT image) and a second CT image (commonly referred to as a "moving" CT image) are subjected to a deformable registration algorithm to obtain a warped second CT image, wherein the warped second CT image is compared with the first CT image to obtain a theoretical deformation. Accordingly, the terms "warped image," "warped CT image" "warped second CT image" and the like refer to an image obtained by subjected a moving image (i.e. the CT image that has been deformed relative to the fixed image) to a deformable registration method. In some embodiments, the deformable registration method produces a warped image based on the moving image such that the resulting warped image is more similar to the fixed image than the moving image. A variety of deformable registration methods are known and are useful in the present invention, including but not limited to the Lucas-Kanade method (Lucas, B. D., & Kanade, T., 1981, in: PROC. IMAGING UNDERSTANDING WORKSHOP (1981), pp. 121-130), the original Horn and Schunck method (Horn, B. K. P., & Schunck, B. G., 1981, *Artif. Intell.* 17:185-203), the inverse consistency Horn and Schunck method as known in the art, the iterative optical flow method (Barron, J. L., et al., 1994, *Int. J. Comput. Vis.* 12:43-77), the fast iterative optical flow method, the symmetric force demons method (Thirion, J. P., 1998, *Med. Image Anal.* 2:243-260; Rogelj, P., et al., 2006, *Med. Image Anal.* 10:484-493), the fast demons method (Wang, H., et al., 2005, *Phys. Med. Biol.* 50:2887-2905), the fast demons method with elastic regularization as known in the art, and the free-form via calculus of variations method (Lu, W. G., et al., 2004, *Phys. Med. Biol.* 49:3067-3087).

A "theoretical deformation" refers to a difference detected between a first position on a first CT image and the corresponding position on a warped second CT image.

The terms "deformable registration" and the like refer, as customary in the art, to a process of transforming different sets of data, e.g., computerized tomography (CT) data, into one coordinate system. Methods of deformable registration are known in the art and/or described herein.

The terms "similarity metric" and the like refer to statistical methods well known in the art of deformable registration. Exemplary similarity metrics include "CC" (cross-correlation), "MI" (mutual information), "SAD" (sum of absolute differences), "SSD" (sum of squared differences) and the like.

The terms "image similarity" and the like refer to the calculated similarity between two images, e.g., fixed and moving images, fixed and warped images, moving and warped images, and the like, as determined by methods known in the art and described herein. In one embodiment, image similarity is calculated by the sum of squared differences (SSD) similarity metric, employing equation: $SSD = \sum_{i=1}^{N}(W_i - F_i)^2$ (Eqn. 1). In this equation, $W_i$ and $F_i$ are the intensities of the warped and fixed images, respectively, as customarily employed in the art. Without wishing to be bound by any theory, it is believed that if a deformation algorithm focuses only on image similarity, then unphysical deformations can appear in the warped image. Accordingly, a penalty function P="similarity"+λ●"regularization" (Eqn. 2) can be employed as known in the art to reduce unphysical deformation. In Eqn. 2, "similarity" is calculated as described herein, e.g., SSD method, the "regularization" term penalizes non-smooth deformations, and the parameter "λ," is optimized to provide an optimal balance between the penalty terms. In one embodiment, the regularization term has the form of Eqn. 3, $$R = \sum_i \sum_a \sum_b \left( \frac{\partial^2 \vec{D}}{\delta x_a \delta x_b} \right)^2, \quad (Eqn. 3)$$

wherein index i spans all points in the compared images, indices a and b span the three spatial coordinates of the images, and vector D is the deformation vector, as known in the art. An "image similarity value" is a numerical value for an image similarity calculation between two images.

A "measured optical deformation" refers to a difference measured between a first position of an optically detectable non-radiopaque marker(s) on a first optical image and a second position of the corresponding optically detectable non-radiopaque marker on a second optical image.

"Theoretical deformations" in the context of CT images refers to deformations predicted by a method for deformable registration.

The terms "radiographic phantom material," "phantom material" and the like refer to materials which mimic corresponding tissues, structures, and the like in a subject. Accordingly, "bony phantom material" mimics e.g., bone, enamel, cartilage and the like, and "soft phantom material" mimics e.g., deformable tissue in a subject, e.g., organs, vasculature, and the like. It is understood that soft phantom material disposed within a phantom as described herein can include a plurality of distinct soft phantom material elements, e.g., soft phantom materials which mimic the radiographic characteristics of fat, muscle, fat-muscle intermediate, or any combination thereof. Material useful for soft phantom material includes urethane rubber and the like. Exemplary soft phantom material includes VytaFlex® 10, VytaFlex® 20, VytaFlex® 30, VytaFlex® 40, VytaFlex® 50, VytaFlex® 60 (Smooth-On, Inc., Easton, Pa.), and the like. It is understood that the flexibility of soft phantom material, e.g., urethane rubber, can be modulated by a variety of methods during manufacture, including e.g., addition of SO-FLEX® flexibilizer (Smooth-On, Inc. Easton, Pa.). Also useful for soft phantom material are TX Products (e.g., TX-150 and TX-151) (Balmar, LLC, Lafayette, La.). It is further understood that bony phantom material can include a plurality of distinct bony phantom material elements, e.g., bony phantom materials which mimic the radiographic characteristics of bone, enamel, cartilage, or any combination thereof. Material useful for bony phantom material as described herein includes urethane plastic and the like. Specific bony phantom material includes Gammex 450 (Gammex, Inc., Middleton, Wis.), and Smooth-Cast® 300 and 320 Series (Smooth-On, Inc., Easton, Pa.), Smooth-Cast® 325, Smooth-Cast® 380, Smooth-Cast® 385, and the like. The radiographic properties (e.g., Hounsfield units) of phantom material can be modulated by the addition of radiopaque material (e.g., brass powder, and the like) during manufacture.

The term "deformable registration error metric" refers to a description, e.g., depiction, enumeration or the like, of the differences between the measured optical deformation and the theoretical deformation predicted by a method for deformable registration between a set of CT images, as described herein.

The term "radiopaque marker" refers in the customary sense to a material which can be observed in a CT scan. The term "non-radiopaque markers" refers to a material which is not substantially observed in a CT scan (e.g., the presence of the non-radiopaque marker does not substantially influence the performance of a deformable registration method or the resulting theoretical deformation). An "optically detectable non-radiopaque marker," as used herein, means a non-radiopaque marker that is detectable using a light detection device, such as an optical camera. Optically detectable non-radiopaque marker are visible when the non-deformed radiographic phantom or the deformed radiographic phantom is viewed, e.g., by an observer or an optical detection device such as a digital camera.

II. Methods

In a first aspect, there is provided a method of detecting a difference between a measured optical deformation of a radiographic phantom pair and a theoretical deformation of the radiographic phantom pair. The method includes (i) comparing a first optical image of a non-deformed radiographic phantom to a second optical image of a deformed radiographic phantom thereby obtaining a measured optical deformation. The method further includes (ii) performing a deformable registration method between a first computerized tomography (CT) image of the non-deformed radiographic phantom and a second CT image of the deformed radiographic phantom using a deformable registration algorithm thereby obtaining a theoretical deformation. The method further includes (iii) comparing the measured optical deformation with the theoretical deformation thereby determining a difference between the measured optical deformation and the theoretical deformation.

In one embodiment, there is provided a method of detecting a difference between a measured optical deformation of a radiographic phantom pair and a theoretical deformation of the radiographic phantom pair. The method includes: (a) receiving a first optical image of a non-deformed radiographic phantom and a second optical image of a deformed radiographic phantom at a system processor. The method further includes: (b) calculating a comparison of the first optical image of the non-deformed radiographic phantom with the second optical image of the deformed radiographic phantom at the system processor, hereby obtaining a measured optical deformation. The method further includes: (c) performing a deformable registration method between a first computerized tomography (CT) image of the non-deformed radiographic phantom and a second CT image of the deformed radiographic phantom using a deformable registration algorithm thereby obtaining a theoretical deformation. The method further includes (d) calculating a comparison of the measured optical deformation with the theoretical deformation at the system processor, thereby determining a difference between the measured optical deformation and the theoretical deformation.

In one embodiment, the system processor is, e.g., a desktop computer, workstation, laptop computer, or other computer platform with sufficient resources to perform the processing functions described herein. In one embodiment, the system processor includes hardware elements that can be electrically coupled via a bus (or may otherwise be in communication, as appropriate). The hardware elements can include one or more central processor units (CPUs), including without limitation one or more general-purpose processors and/or one or more special-purpose processors or processor cores. The hardware elements can further include one or more input devices, such as a computer mouse, a keyboard, a touchpad, and/or the like for providing user input; and one or more output devices, such as a flat panel display device, a printer, visual projection unit, and/or the like. The system processor may further include (and/or be in communication with) one or more storage devices, which can include, without limitation, local and/or network accessible storage and/or can include, without limitation, a disk drive, a drive array, an optical storage device, solid-state storage device such as a random access memory ("RAM"), and/or a read-only memory ("ROM"), which can be programmable, flash-updateable, and/or the like.

Further to any embodiment described above, in one embodiment the first optical image and the second optical image are obtained prior to step (i). In one embodiment, the first optical image and the second optical image are obtained prior to step (a).

Further to any embodiment described above, in one embodiment the first CT image and the second CT image are obtained prior to step (ii). In one embodiment the first CT image and the second CT image are obtained prior to step (c).

Further to any embodiment described above, in one embodiment the non-deformed radiographic phantom and the deformed radiographic phantom are constructed prior to step (i). In one embodiment the non-deformed radiographic phantom and the deformed radiographic phantom are constructed prior to step (a).

Further to any embodiment described above, in one embodiment, the non-deformed radiographic phantom and the deformed radiographic phantom each include a radiographic phantom material interposed between two parallel plates, the radiographic phantom material includes a soft phantom material and a plurality of optically detectable non-radiopaque markers in spatial communication with the soft phantom material. In one embodiment, the radiographic phantom material further includes a bony phantom material. The term "spatial communication" refers to a physical communication such that movement of the soft phantom material (or bony phantom material that moves the soft phantom material) results in a corresponding movement of one or more optically detectable non-radiopaque markers.

In one embodiment, at least part of the optically detectable non-radiopaque markers are disposed on the surface (e.g. on top) of the soft phantom material or the bony phantom material. The term "on top" or "on the surface" in this context refers to a positioning of the optically detectable non-radiopaque markers such that they are not substantially embedded within the soft phantom material. In one embodiment, at least part of the optically detectable non-radiopaque markers are disposed within (e.g. embedded within) the soft phantom material or the bony phantom material. In one embodiment, at least part of the optically detectable non-radiopaque markers are disposed on top of the soft phantom material or the bony phantom material, and at least part of the optically detectable non-radiopaque markers are disposed within the soft phantom material or the bony phantom material.

In one embodiment, the optically detectable non-radiopaque markers are visible by virtue of having a color, texture, or other visible characteristic which differs from the underlying soft phantom material or bony phantom material upon which the optically detectable non-radiopaque markers are positioned. In one embodiment, the optically detectable non-radiopaque markers have a different color than the underlying soft phantom material or bony phantom material upon which the optically detectable non-radiopaque markers are positioned. In one embodiment, the optically detectable non-radiopaque markers are fluorescent or phosphorescent. In one embodiment, the optically detectable non-radiopaque markers are disposed in a pattern, e.g., an evenly spaced grid pattern or the like. In one embodiment, the density of optically detectable non-radiopaque markers is 1 per square mm, 2 per square mm, 3 per square mm, 4 per square mm, 5 per square mm, 6 per square mm, 7 per square mm, 8 per square mm, 9 per square mm, 10 per square mm, or even greater. In one embodiment, the density of optically detectable non-radiopaque markers is 1 per square cm, 2 per square cm, 3 per square cm, 4 per square cm, 5 per square cm, 6 per square cm, 7 per square cm, 8 per square cm, 9 per square cm, 10 per square cm, 20 per square cm, 30 per square cm, 40 per square cm, 50 per square cm, 60 per square cm, 70 per square cm, 80 per square cm, 90 per square cm, 100 per square cm, or even greater. In one embodiment, optically detectable non-radiopaque markers are provided in a grid pattern having a marker disposed every 1 mm, 2 mm, 3 mm, 4 mm, 5 mm, 6 mm, 7 mm, 8 mm, 9 mm, 10 mm, or even greater spacing, in orthogonal (e.g., x and y) directions. In one embodiment, optically detectable non-radiopaque markers are provided in a pattern with a density of about 1-100 per square cm, 1-90 per square cm, 1-80 per square cm, 1-70 per square cm, 1-60 per square cm, 1-50 per square cm, 1-40 per square cm, 1-30 per square cm, 1-20 per square cm, 1-10 per square cm, 1-9 per square cm, 1-8 per square cm, 1-7 per square cm, 1-6 per square cm, 1-5 per square cm, 1-4 per square cm, 1-3 per square cm, 1-2 per square cm, or even 1 per square cm. Absent express indication otherwise, the term "about" in the context of a numeric value represents the nominal value ±10%. In some related embodiments, the optically detectable non-radiopaque markers are space evenly (e.g. in even orthogonal directions) where a density is provided.

In one embodiment, the deformed radiographic phantom further includes a deformation element within said soft phantom material. In one embodiment, the deformation element is a catheter balloon lumen. In one embodiment, the deformation element is the tip of a catheter balloon. In one embodiment, a catheter balloon deforms a radiographic phantom upon partial or full inflation.

Further to any embodiment disclosed above, in one embodiment the method further includes adjusting the deformable registration method to decrease the difference between the measured optical deformation and the theoretical deformation. In one embodiment, the adjusting includes changing the deformable registration algorithm. In one embodiment, the changing the deformable registration algorithm includes evaluating the image similarity of the fixed and warped image in comparison to the statistical noise inherent to the CT images. In one embodiment, changing includes increasing or decreasing an image similarity value assigned by the deformable registration algorithm based on the evaluation. In other embodiment, the changing includes increasing CT image noise levels allowed by the deformable registration algorithm.

In another aspect, there is provided a method for verifying a method for deformable registration. The method includes obtaining a first optical image and a first computerized tomography (CT) image of a non-deformed radiographic phantom. The method further includes obtaining a second optical image and a second CT image of a deformed radiographic phantom. The method further includes comparing the second optical image with the first optical image, thereby obtaining a measured optical deformation. The method further includes performing a deformable registration method between the second CT image and the first CT image, thereby obtaining a theoretical deformation. The method further includes comparing the measured optical deformations with the theoretical deformation, thereby verifying the method for deformable registration.

In one embodiment, the method includes receiving a first optical image and a first computerized tomography (CT) image of a non-deformed radiographic phantom at a system processor. The method further includes receiving a second optical image and a second CT image of a deformed radiographic phantom at the system processor. The method further includes calculating the deformation of the second optical image with respect to the first optical image on the system processor, thereby obtaining a measured optical deformation. The method further includes performing a deformable registration method between the second CT image and the first CT image, thereby obtaining a theoretical deformation. The method further includes calculating a comparison of the measured optical deformations with the theoretical deformation at the system processor, thereby verifying the method for deformable registration.

In some embodiments, the non-deformed radiographic phantom includes two parallel plates having radiographic phantom material interposed between the plates. The radiographic phantom material includes bony phantom material, soft phantom material, and surface markers attached to the soft phantom material. In some embodiments, the parallel plates are transparent or substantially transparent. The terms "substantially transparent" and the like refer to sufficient transparency to observe a feature of the phantom, e.g., a surface marker. In some embodiments, the parallel plate through which the surface marker is observed is transparent or substantially transparent.

In some embodiments, the deformed radiographic phantom includes two parallel plates having radiographic phantom material interposed between the plates. In some embodiments, the parallel plates are transparent or substantially transparent. In some embodiments, the parallel plate through which the surface marker is observed is transparent or substantially transparent.

Further to any of the methods or devices described herein, in some embodiments two separate radiographic phantoms are employed, i.e., a "radiographic phantom-pair," wherein the only substantive difference, in the context of an optical or CT image, between the members of the pair is a deformation. The term "substantive difference" in this context means that the members of the phantom differ only in the deformation and the effects thereof (e.g., displacement of tissue adjacent to the deformation). In some embodiments, a single radiographic phantom is employed, which single radiographic phantom can undergo deformation in order to model a corresponding deformation observed in a subject, e.g., growth or reduction of a tumor, inflation or deflation of a bladder or other cavity, and the like.

Accordingly, in some embodiments, the non-deformed radiographic phantom and the deformed radiographic phantom are distinct devices having substantially identical placements of the bony phantom material, substantially identical amounts of the soft phantom material, and substantially identical placement of surface markers.

In some embodiments, the soft phantom material further comprises at least one inflatable catheter balloon tip and a lumen disposed within the soft phantom material. The lumen has a distal end in fluidic contact with the at least one inflatable catheter balloon tip and a proximal end in fluidic contact with the distal end of the lumen, whereby fluid introduced at the proximal end of the lumen inflates and thereby deforms the at least one inflatable catheter balloon tip. In some embodiments, fluid is injected into the proximal end in order to mimic an enlargement of a tissue, e.g., a tumor, by the enlargement of the inflatable catheter balloon tip. In some embodiments, fluid is withdrawn from the proximal end in order to mimic a reduction in the size of a tissue, e.g., a tumor, by the reduction in the size of the inflatable catheter balloon tip.

Further to any method or devices described herein, in some embodiments, at least one of the two parallel plates further includes a plurality of radiopaque markers. In some embodiments, the soft phantom material further includes a plurality of radiopaque markers. Further to any method or device described herein, in some embodiments the radiopaque markers are fluorescent or phosphorescent. In some embodiments, the soft phantom material further includes a plurality of non-radiopaque markers.

In another aspect, there is provided a method for identifying a method for deformable registration. The term "identifying" in this context refers to determining a comparatively better method of deformable registration. The method includes obtaining a first optical image and a first CT image of a non-deformed radiographic phantom. The method further includes obtaining a second optical image and a second CT image of a deformed radiographic phantom. The method further includes comparing the second optical image to the first optical image, thereby obtaining a measured optical deformation. The method further includes performing a first method for deformable registration between the second CT image and the first CT image, thereby obtaining a first theoretical deformation. The method further includes comparing the measured optical deformation with the first theoretical deformation, thereby obtaining a first deformable registration error metric. The method further includes performing a second method for deformable registration between the second CT image and the first CT image, thereby obtaining a second theoretical deformation. The method further includes comparing the measured optical deformation with the second theoretical deformation, thereby obtaining a second deformable registration error metric. The method further includes comparing the first deformable registration error metric with the second deformable registration error metric, thereby identifying a method for deformable registration In one embodiment, the method includes receiving a first optical image and a first CT image of a non-deformed radiographic phantom at a system processor. The method further includes receiving a second optical image and a second CT image of a deformed radiographic phantom at the system processor. The method further includes calculating a comparison of the second optical image with respect to the first optical image on the system processor, thereby obtaining a measured optical deformation. The method further includes performing a first method for deformable registration between the second CT image and the first CT image, thereby obtaining a first theoretical deformation. The method further includes calculating a comparison of the measured optical deformation with the first theoretical deformation on the system processor, thereby obtaining a first deformable registration error metric. The method further includes performing a second method for deformable registration between the second CT image and the first CT image, thereby obtaining a second theoretical deformation. The method further includes calculating a comparison of the measured optical deformation with the second theoretical deformation at the system processor, thereby obtaining a second deformable registration error metric. The method further includes calculating a comparison of the first deformable registration error metric with the second deformable registration error metric on the system processor, thereby identifying a method for deformable registration.

In another aspect, there is provided a method for testing for quality assurance of a method for deformable registration. The method includes obtaining a first optical image and a first CT image of a non-deformed radiographic phantom. The method further includes obtaining a second optical image and a second CT image of a deformed radiographic phantom. The method further includes comparing the second optical image to the first optical image, thereby obtaining a first measured optical deformation. The method further includes performing a method for deformable registration between the second CT image and the first CT image, thereby obtaining a first theoretical deformation. The method further includes comparing the first measured optical deformation with the first theoretical deformation, thereby obtaining a reference deformable registration error metric. The method further includes obtaining a third optical image and a third CT image of a non-deformed radiographic phantom under conditions where the third CT image may have changed relative to the first CT image. The term "may have changed" in this context refers to any of a variety of changes in the observable conditions, including e.g., changes in CT instrument settings, software and the like, changes in age or physical condition of the subject, and the like. The method further includes obtaining a fourth optical image and a fourth CT image of a deformed radiographic phantom under conditions where the fourth CT image may have changed relative to the second CT image. The method further includes comparing the fourth optical image to the third optical image, thereby obtaining a second measured optical deformation. The method further includes performing the method for deformable registration between the fourth CT image and the third CT image, thereby obtaining a second theoretical deformation. The method further includes comparing the second measured optical deformation with the second theoretical deformation, thereby obtaining a test deformable registration error metric. The method further includes comparing the reference deformable registration error metric with the test deformable registration error metric, thereby testing for quality assurance of a method for deformable registration.

In one embodiment, the method includes receiving a first optical image and a first CT image of a non-deformed radiographic phantom at a system processor. The method further includes receiving a second optical image and a second CT image of a deformed radiographic phantom at a system processor. The method further includes calculating a comparison of the second optical image to the first optical image, thereby obtaining a first measured optical deformation. The method further includes performing a method for deformable registration between the second CT image and the first CT image, thereby obtaining a first theoretical deformation. The method further includes calculating a comparison of the first measured optical deformation with the first theoretical deformation at the system processor, thereby obtaining a reference deformable registration error metric. The method further includes receiving a third optical image and a third CT image of a non-deformed radiographic phantom at the system processor under conditions where the third CT image may have changed relative to the first CT image. The method further includes receiving a fourth optical image and a fourth CT image of a deformed radiographic phantom at the system processor under conditions where the fourth CT image may have changed relative to the second CT image. The method further includes calculating a comparison of the fourth optical image to the third optical image on the system processor, thereby obtaining a second measured optical deformation. The method further includes performing the method for deformable registration between the fourth CT image and the third CT image, thereby obtaining a second theoretical deformation. The method further includes calculating a comparison of the second measured optical deformation with the second theoretical deformation on the system processor, thereby obtaining a test deformable registration error metric. The method further includes calculating a comparison of the reference deformable registration error metric with the test deformable registration error metric, thereby testing for quality assurance of a method for deformable registration.

In another aspect, there is provided a method for improving a method for deformable registration. The method includes obtaining a first optical image and a first CT image of a non-deformed radiographic phantom. The method further includes obtaining a second optical image and a second CT image of a deformed radiographic phantom. The method further includes comparing the second optical image to the first optical image, thereby obtaining a measured optical deformation. The method further includes performing a method for deformable registration between the second CT image and the first CT image, thereby obtaining a theoretical deformation. The method further includes comparing the measured optical deformation with the theoretical deformation, thereby providing a deformable registration error metric. The method further includes identifying regions of error within the deformable registration error metric. The method further includes identifying components of the deformable registration algorithm corresponding to the regions of error within the deformable registration error metric, thereby improving the method for deformable registration.

In one embodiment, the method includes receiving a first optical image and a first CT image of a non-deformed radiographic phantom at a system processor. The method further includes receiving a second optical image and a second CT image of a deformed radiographic phantom at the system processor. The method further includes calculating a comparison of the second optical image to the first optical image, thereby obtaining a measured optical deformation. The method further includes performing a method for deformable registration between the second CT image and the first CT image, thereby obtaining a theoretical deformation. The method further includes calculating a comparison of the measured optical deformation with the theoretical deformation on the system processor, thereby providing a deformable registration error metric. The method further includes identifying regions of error within the deformable registration error metric. The method further includes identifying components of the deformable registration algorithm corresponding to the regions of error within the deformable registration error metric, thereby improving the method for deformable registration.

In another aspect, there is provided a method of minimizing organ risk dose in a treatment region of a radiological treatment of a subject in need thereof, wherein the radiological treatment includes a plurality of radiological dosings. The method includes obtaining a first CT image of the subject prior to a radiological dosing. The method further includes obtaining a second CT of the subject subsequent to the radiological dosing. The method further includes calculating a deformation registration of the first CT image and the second CT image. The method further includes calculating a spatial uncertainty for the deformation registration, thereby providing a dose uncertainty. The method further includes modifying a subsequent radiological dosing based on the dose uncertainty, thereby minimizing organ risk dose. The term "organ risk dose" refers in the customary sense to a level of radiological dosing which would injure an organ, e.g., an organ adjacent to the site of radiological treatment. The term "treatment region of a radiological treatment" refers in the customary sense to the site of radiological treatment and surrounding tissue. The term "radiological dosing" refers in the customary sense to administration of radiation to ameliorate a disease or condition, e.g., to shrink the size of a tumor. The term "spatial uncertainty for the deformation registration" refers to the uncertainty in positioning in 3-dimensional space obtained by a deformation registration procedure. Spatial uncertainty for a deformation registration procedure can be determined by employing a method disclosed herein, e.g., a method using a radiological phantom-pair. The term "dose uncertainty" refers to a metric, e.g., a 3-dimension representation, of the uncertainty of the radiological dosing. Methods for calculating dose uncertainty from spatial uncertainty are known in the art. For example, spatial uncertainty can be multiplied by the gradient of the dose to afford the dose uncertainty. Calculation of the deformation registration employs a method disclosed herein or known in the art. It is understood that uncertainty in radiological dosing can arise from a variety of factors, including e.g., deformation of the target site of the subject during the course of the radiological treatment, change in volume of tissue adjacent to the target site, and the like.

In one embodiment, the spatial uncertainty is determined by (i) comparing a first optical image of a non-deformed radiographic phantom to a second optical image of a deformed radiographic phantom thereby obtaining a measured optical deformation, wherein the non-deformed radiographic phantom and the deformed radiographic phantom mimic the treatment region of the radiological treatment. In a further step (ii), a deformable registration method is conducted between a first computerized tomography (CT) image of the non-deformed radiographic phantom and a second CT image of the deformed radiographic phantom using a deformable registration algorithm, thereby affording a theoretical deformation. In a further step (iii), the measured optical deformation is compared with the theoretical deformation to afford the difference between the measured optical deformation and the theoretical deformation, thereby providing a spatial uncertainty.

III. Apparatus

In another aspect, there is provided a radiographic phantom. The radiographic phantom includes: (i) two parallel plates; and (ii) a radiographic phantom material interposed between the parallel plates, wherein the radiographic phantom material includes a soft phantom material and a plurality of optically detectable non-radiopaque markers in spatial communication with the soft phantom material. In one embodiment, the radiographic phantom further includes a deformation element within the soft phantom material.

In one embodiment, the phantom represents an axial plane of the pelvic anatomy. Urethane plastic serves as the bony anatomy and urethane rubber with three levels of Hounsfield units (HU) is used to represent fat and organs, including the prostate. In one embodiment, an insert such as a plastic insert (e.g. a cylindrical plastic insert or a roughly cylindrical insert) is placed into the phantom to simulate bladder filling. In one embodiment, a deformable element is inflated to simulate bladder filling. Non-radiopaque markers reside on the phantom surface. Optical camera images of these markers are used to measure the positions and determine the deformation from the bladder insert. Eleven different deformable registration techniques are applied to the full- and empty-bladder computed tomography images of the phantom to calculate the deformation. The applied algorithms include those from MIMVISTAT™ Software and Velocity Medical Solutions and 9 different implementations from the Deformable Image Registration and Adaptive Radiotherapy Toolbox (DIRART) for MATLAB™. The distance to agreement between the measured and calculated deformations is used to evaluate algorithm error. Deformable registration warps one image to make it similar to another. The root-mean-square (RMS) difference between the HUs at the marker locations on the empty-bladder phantom and those at the calculated marker locations on the full-bladder phantom is used as a metric for image similarity.

In one embodiment, the radiographic phantom material further includes a bony phantom material. In one embodiment, at least part of the bony phantom material is rigidly attached to at least one of the two parallel plates.

In one embodiment, the radiographic phantom further includes a radiographic encasement substantially enclosing the two parallel plates. In some embodiments, the radiographic phantom includes an encasement designed to minimize imaging artifacts. Without wishing to be bound by any theory, it is believed that if a scan of a phantom is performed without this encasement, imaging artifacts may appear at the abrupt transitions between the phantom parallel plates, e.g., acrylic sheets, and air. Subjects for CT scans, e.g., physiological subject including humans, typically do not possess such abrupt transitions. Accordingly, CT machines have not been built to properly scan and/or account for such abrupt transitions.

In another aspect, there is provided a non-deformed radiographic phantom, which includes two parallel plates having radiographic phantom material interposed therebetween. The radiographic phantom material may include bony phantom material, soft phantom material and surface markers attached to the soft phantom material (and optionally the bony phantom material). In some embodiments, the bony phantom material is rigidly attached to at least one of the two parallel plates. In some embodiments, the bony phantom material is not rigidly attached to at least one of the two parallel plates. In some embodiments, at least part of the bony phantom material is rigidly attached to at least one of the two parallel plates. In some embodiments, one or more of the plurality of elements forming the bony phantom material is rigidly attached to at least one of the two parallel plates. In some embodiments, one or more of the plurality of elements forming the bony phantom material is not rigidly attached to at least one of the two parallel plates. In one embodiment, the non-deformed radiographic phantom further includes a radiographic encasement substantially enclosing the two parallel plates.

In another aspect, there is provided a deformed radiographic phantom, which includes two parallel plates having radiographic phantom material interposed therebetween. The radiographic phantom material includes bony phantom material, soft phantom material, and surface markers attached to the soft phantom material. In some embodiments, the bony phantom material is rigidly attached to at least one of the two parallel plates. In some embodiments, the bony phantom material is not rigidly attached to at least one of the two parallel plates. In some embodiments, at least part of the bony phantom material is rigidly attached to at least one of the two parallel plates. In some embodiments, one or more of the plurality of elements forming the bony phantom material is rigidly attached to at least one of the two parallel plates. In some embodiments, one or more of the plurality of elements forming the bony phantom material is not rigidly attached to at least one of the two parallel plates.

In some embodiments, the deformed radiographic phantom further includes a radiographic encasement substantially enclosing the parallel plates.

In another aspect, there is provided a computerized tomography apparatus which includes: (i) a CT scanner comprising an X-ray source and an X-ray detector; and (ii) a radiographic phantom between the X-ray source and the X-ray detector, wherein the radiographic phantom comprises (a) two parallel plates; and (b) a radiographic phantom material interposed between the parallel plates, wherein the radiographic phantom material comprises a soft phantom material and a plurality of optically detectable non-radiopaque markers in spatial communication with the soft phantom material.

In one embodiment, the radiographic phantom material further includes a bony phantom material. In one embodiment, at least part of the bony phantom material is rigidly attached to at least one of the two parallel plates. In one embodiment, the computerized tomography apparatus further includes a radiographic encasement substantially enclosing the two parallel plates. In one embodiment, the computerized tomography apparatus further includes a deformation element with the soft phantom material.

IV. EXAMPLES

Example 1

Quantitative Verification of Deformation Algorithms Using a Two-Dimensional Deformable Phantom Introduction and Description of Example Purpose.

The incorporation of deformable image registration into the treatment planning process is rapidly advancing. For this reason, the methods used to verify the underlying deformation algorithms must continue to evolve. Thus, there is provided a two-dimensional deformable phantom, which circumvents several of the shortcomings in the current verification methods, useful for improving these techniques.

General Methods.

The phantom represents a single plane of the anatomy of a patient, e.g., in the region of the head and neck, knee, arm, pelvis, and the like of a patient. Inflation of a balloon catheter inside the phantom simulates tissue deformations from tumor growth. Non-radiopaque markers reside on the surface of the deformable anatomy and are visible through an acrylic plate, which enables an optical camera to measure their positions. CT and camera images of the phantom are acquired before and after its deformation. The measured deformations from the camera images are then directly compared to those predicted by a deformation algorithm using several different similarity metrics. Additionally, the measured deformations from the phantom are interpolated to the pixel positions of an anatomically-similar patient CT image. This interpolated deformation is then applied to the image to create a simulated deformation, which is compared to the deformable registration predictions.

Description of Apparatus.

In some embodiments, the deformation phantom represents a single two-dimensional slice of the body. Although the phantom is constructed in three dimensions, it and its deformations are symmetric with respect to the z-direction, making it function as a two-dimensional system. In some embodiments, the phantom consists of two parallel acrylic plates, between which the phantom material is placed. Gammex 450 tissue-equivalent material is used, e.g., for the bony anatomy and is rigidly attached to the acrylic plates. Mixing of TX-151 solidifying powder (Balmar, LLC, Lafayette, La.) with water produces, e.g., the deformable material of the phantom. This deformable material is then fastened to the bony anatomy with an elastic band. A strip of polycarbonate creates a void in the deformable anatomy that represents, e.g., the pharynx. In addition, lubricant is applied to the acrylic plates to make them function as frictionless surfaces. A 30 cc silicone Foley catheter acts as the shrinking tumor. This balloon catheter is filled with a diluted barium sulfate suspension, which increases its measured Hounsfield units by 3% beyond that of the deformable tissue. FIG. 1 displays an image of the assembled prototype.

A 1/16-inch hole punch creates the surface markers from a thin sheet of optically-opaque plastic. These markers are then attached, in a grid, to the initial z slice of the phantom material with super glue. In addition, gold fiducial markers are attached to the inside of the initial acrylic plate. These fiducials are visible to both the digital camera and to the CT scanner, which allows for a position calibration between them.

Data Acquisition.

To test the accuracy of a deformation algorithm, CT and optical camera images of the phantom are acquired before and after its deformation. The black color of the surface markers creates a sharp contrast against the pink deformable anatomy. Software uses this contrast to locate the markers on the camera images and to calculate their mean positions. To test the random error of this measurement, multiple pictures of the setup are taken after realigning the camera. This test yields a 0.24 mm standard deviation for the measurement uncertainty. In addition, rulers that line the inside of the front acrylic plate indicate that the nonlinearity of the image pixel positions is at or below the pixel size (0.13 mm). These errors are smaller than the transverse size of the CT pixels (0.98 mm). Thus, the pixilation of the CT dominates the error in the matching between the CT and camera images.

The Siemens Corporate Research 3D Deformable Registration software, which utilizes a free-form B-splines deformation algorithm, is used to predict the warping between the two CT images. To maintain the two-dimensional nature of the verification technique, this software is applied only on the initial CT slice, which is directly underneath the front acrylic plate. Four different similarity metrics are used from the software: cross correlation (CC), mutual information (MI), sum of absolute differences (SAD), and sum of squared difference (SSD). The predicted deformations from the software is then applied to the positions of the surface markers and compared to the actual deformations, as measured on the digital camera images. Since the phantom represents a shrinking tumor, the terms before and after correspond to an inflated and deflated catheter, respectively.

Deformation of Patient Images.

The phantom represents a transverse slice of an actual patient CT image. This allowed the phantom to test its complement with the patient image. For each pixel of the patient CT image, the three closest phantom markers are located. The deformation values for these markers are then weighted, by the inverse of their separation from the pixel, and averaged to determine the pixel deformation. This usage of the three closest markers creates domains in the determined deformation, which are unphysical. For this reason, the results are then blurred with a Gaussian in both directions. The resulting deformation field is then applied to the original patient CT image to produce a deformed one and compared to algorithm predictions.

Results

Figure 2A:
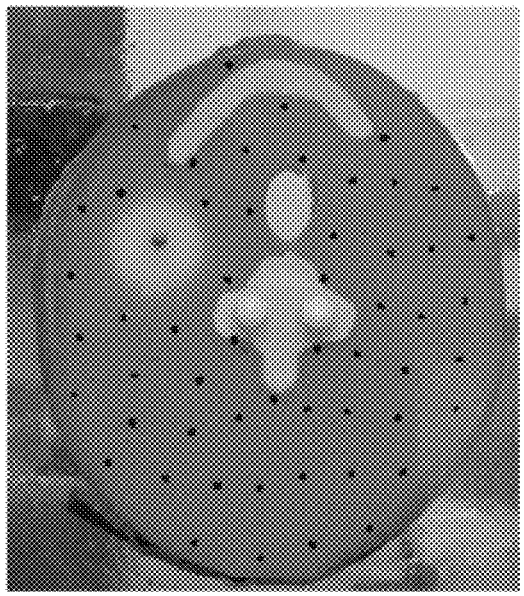
FIGS. 2A-2C. Depicted are a phantom described herein with an inflated (FIG. 2A) and deflated (FIG. 2B) catheter, where the markers are indicated by visible indicia.
Figure 2B:
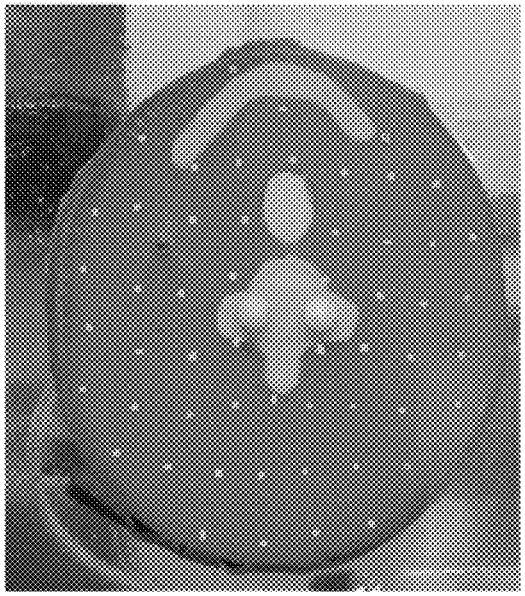
Figure 2C:
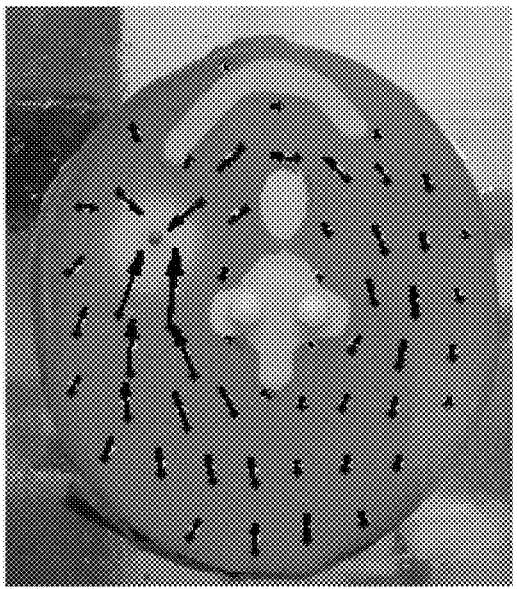
Figure 3A:
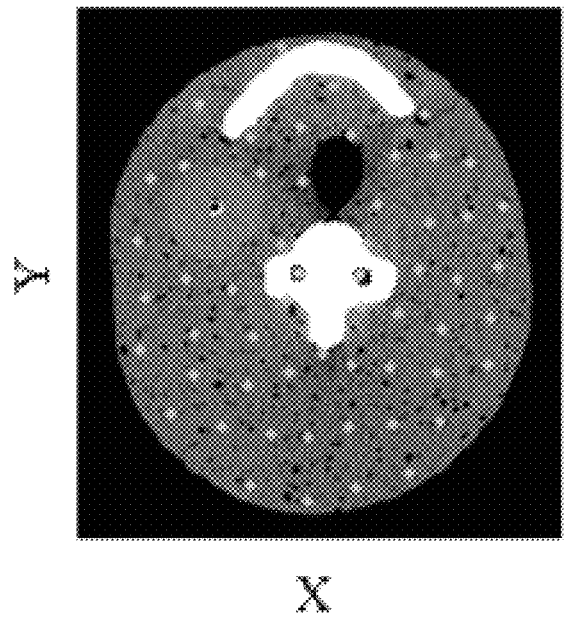
FIGS. 3A-3B depict CT images of the phantom with an inflated (FIG. 3A) and deflated (FIG. 3B) catheter, where the marker locations appear as dots.
Figure 3B:
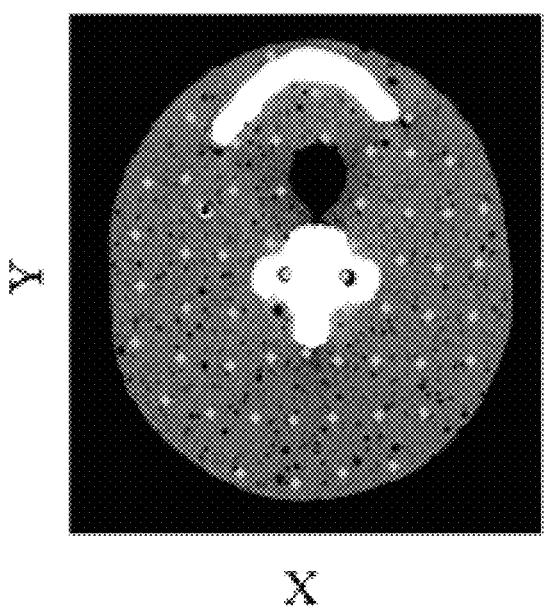
Figure 4A:
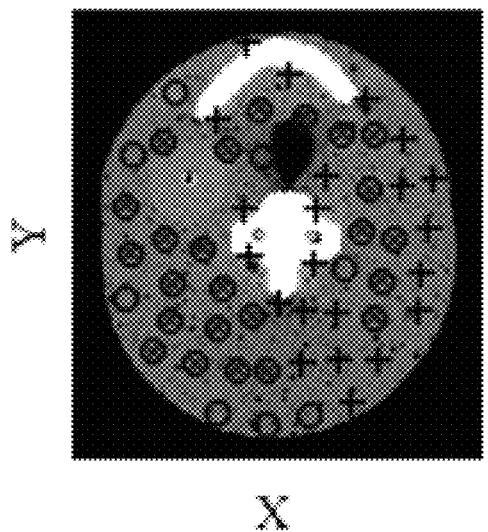
FIGS. 4A-4C depict a comparison of the measured and predicted deformations for four different similarity metrics: CC, MI, SAD, and SSD. The "+" signs and the circles denote whether a surface marker was deformed by more than or less than 3 mm, respectively. An "X" denotes a marker with a predicted deformation that is separated by more than 3 mm from its actual deformation.
Figure 4B:
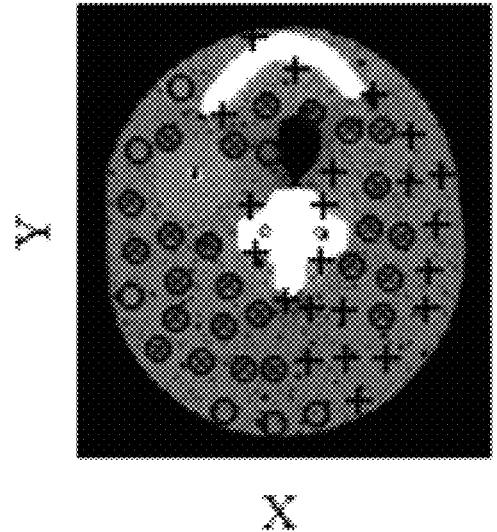
Figure 4C:
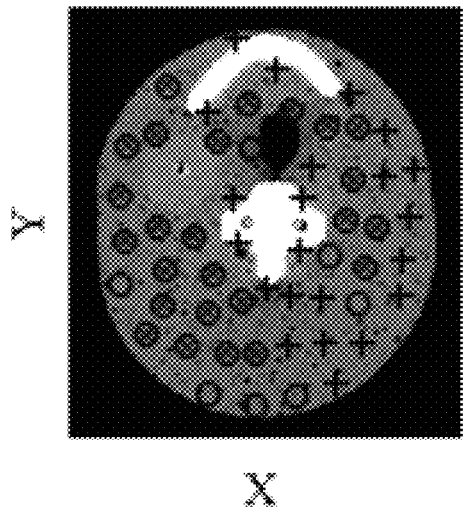

FIGS. 2a and 2b display the before and after camera images of the phantom. The determined deformation field for these images appears in FIG. 2c. FIGS. 3A-3B then show the corresponding CT images. The deformation algorithm is applied to these CT images to predict the warping between them. FIGS. 4A-4C display a comparison of the measured and predicted deformations. Of the 54 surface markers, 32 are deformed by more than 3 mm. After the application of the similarity metrics CC and SSD, 24 of these 32 points (75%) are separated by more than 3 mm from their actual positions. In comparison, MI and SAD have at least a 3 mm deformation error for 25 of the 32 points (78%).

Figure 5A:
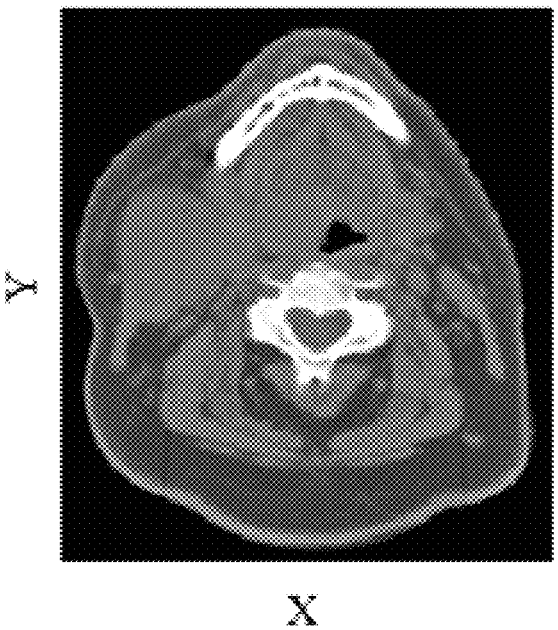
FIGS. 5A-5B depict the original CT slice of the subject (FIG. 5A) and the corresponding deformed CT slice (FIG. 5B).
Figure 5B:
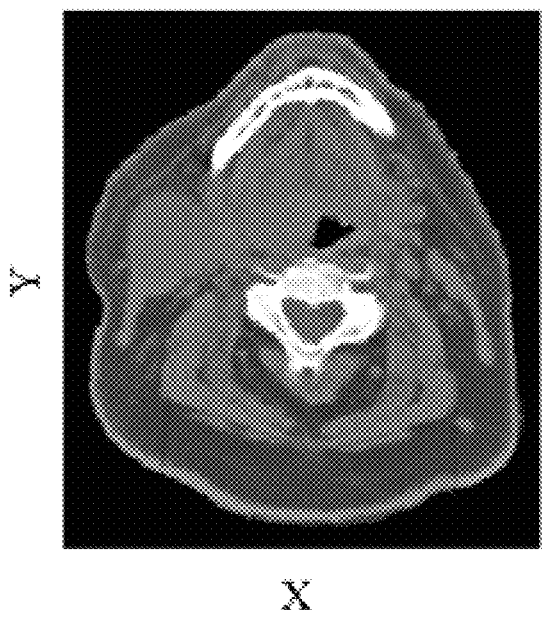
Figure 6A:
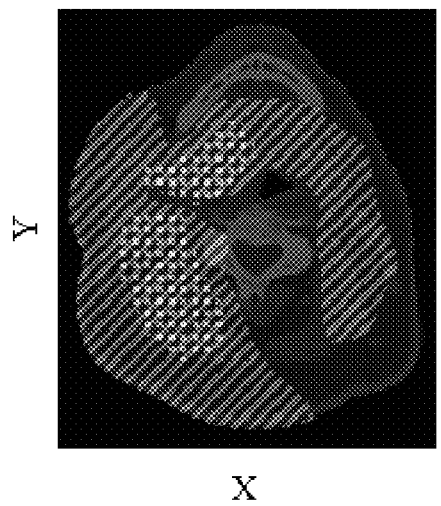
FIGS. 6A-6D depict a comparison of the applied deformation to predictions from four similarity methods: CC (FIG. 6A), MI (FIG. 6B), SAD (FIG. 6C), and SSD (FIG. 6D). Legend for FIGS. 6A-6D: observed deformation (diagonal stripes); deformation error greater than 3 mm (crosshatched).
Figure 6B:
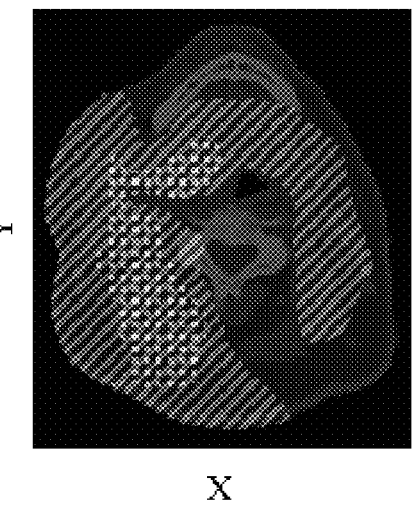
Figure 6C:
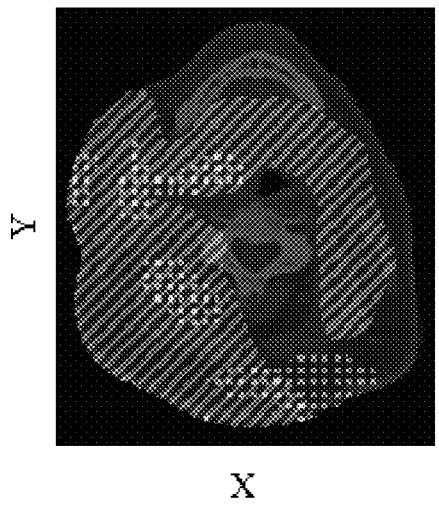
Figure 6D:
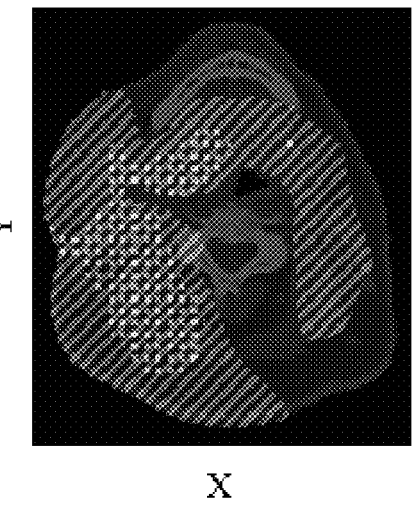

FIG. 5 displays the original patient CT image and the corresponding deformed one. Since the catheter position matches that of the patient tumor, its deflation causes the tumor in the CT to shrink. FIGS. 6A-6D show a comparison of the applied and predicted deformations for the patient CT image. The ratios of the number of pixels with more than a 3 mm deformation error over those that are deformed by more than 3 mm are 25%, 27%, 27%, and 31% for CC, MI, SAD, and SSD, respectively.

In summary, the balloon catheter deforms 32 out of the 54 surface markers by more than 3 mm. Different deformation fields result from the assortment of similarity metrics. After applying deformable registration with the most accurate similarity metric, 24 of the 32 points (75%) are still separated by more than 3 mm from their actual positions. The deformation results improve with the use of the simulated CT deformations. The best results reduced the ratio of the number of points with more than a 3 mm deformation error over those that are deformed by more than 3 mm to 25%.

Discussion

From the results achieved with the CT images of the phantom, it was observed that most of the surface markers that are both deformed by more than 3 mm and corrected to within 3 mm of their actual positions are near sharp transitions in electron density. Thus, the deformable registration is not as accurate in the middle of deformable tissue, where the electron density is fairly homogenous. Conversely, this same region of the patient CT image has local electron density variations, which enables substantially more accurate deformation predictions.

The phantom design is adaptable to represent the imaging and elastic properties of any two-dimensional slice of the body. In addition, the source of deformation can be tailor-made to imitate various tissue distortions of this slice, for instance, tumor shrinking, weight loss, catheter insertion, bladder filling, and probe insertion. As an example, the phantom could be used to study the deformations caused by catheter insertion during brachytherapy. This phantom could represent a slice of the pelvis. Then, the insertion of catheters, or their two-dimensional analogue, would generate phantom distortions. This same phantom could also be used to study the deformations caused by the insertion of a rectal probe for ultrasound. It is, however, important that special consideration is taken when choosing the location of a two-dimensional slice. The body deforms in three dimensions, but some planes would be well represented by a two-dimensional system.

A two-dimensional phantom could be used to study the performance of different algorithms as a function of deformation type and amplitude for a variety of anatomical locations. In addition to evaluating which algorithm works the best for each location, this verification technique could elucidate the underlying reason and provoke further developments to the deformable registration process. The use of these phantoms could, however, extend beyond just research.

Methods for deformable registration are increasingly found in clinical workstations. There are many different deformation algorithms, and as FIGS. 6A-6D demonstrate, variations in these algorithms can greatly influence the predicted deformation. Errors in these predictions could inadvertently affect the quality of a radiation treatment. Thus, just as any other part of the treatment process, the deformation algorithms require quality assurance techniques. For example, an institution could posses a pair of before and after phantoms. Except for the size of the deformation source, these phantoms would be identical or substantially identical. A technician could scan the before and after phantoms and then apply deformable registration to the corresponding images. The resulting deformation predictions would then be compared directly to the measured deformations, thus providing quality assurance for the method of deformable registration.

Conclusion

The two-dimensional deformable phantom is a new method of quantitatively verifying deformation algorithms that avoids problems with the existing techniques. These phantoms serve, e.g., as the quality assurance complement to the rapidly advancing implementation of deformable registration. The reduction of the deformable anatomy to a two-dimensional system allows for the use of non-radiopaque markers, which do not influence deformation algorithms. This is an advantage of this verification technique. The results presented here demonstrate the utility of the phantom for verifying deformation algorithms and the ability to determine which is the most accurate. They also indicate that the phantom benefit from more electron density heterogeneity.

Example 2

Discrete Radiographic Phantoms

Introduction

Two important categories for the use of deformation phantoms are for research and for routine quality assurance. For pure research uses, a radiographic phantom as described above works well. For example, a researcher can apply deformations of various types and magnitudes and measure the resulting deformation field. These data can then be directly compared to deformation prediction for CT scans of the device.

However, without wishing to be bound by any theory, it is believed to be difficult to make the deformations precisely reproducible; thus, it is important that the deformation is measured at the same time that the scans are acquired. For pure research uses, the time needed to determine the deformation would be allowable; however, for routine quality assurance uses, the process admits to methods and devices to reduce the time required.

Accordingly, we explored another embodiment of the phantom. This embodiment relies on the use of a pair of phantoms, representing before and after deformation. Except for the size of the deformation source, these phantoms are substantially identical. In contrast to the embodiments described above, these phantoms are fixed, which ensures a constant deformation between them. Thus, the deformation between the phantoms only needs to be determined once.

Figure 7:
FIG. 7 depicts the constructed before and after phantoms of a phantom-pair, which represent deformation from bladder filling.

A technician can scan the before and after phantoms and then apply deformation algorithms to the corresponding images. The resulting deformation predictions can then be compared directly to the measured deformations. This allows the technician, e.g., the operator of a CT instrument at e.g., an institution, clinic, or the like, to monitor how any changes in image quality, CT instrument settings, and the like, affects the ability to determine a deformation. FIG. 7 shows the constructed before and after phantoms, which represent deformation from bladder filling.

Design Considerations

Although the radiographic phantoms described in Example 1 and Example 2 may be used advantageously in different contexts, the features of either may be advantageously used in the other.

Phantom Material.

In some embodiments, the bony anatomy is constructed from a urethane plastic and the deformable anatomy is made from a urethane rubber. Different parts of the deformable anatomy have different recipes to make them resemble their intended anatomy on a CT scan. The parts of the anatomy in this context may be divided into four categories: bone, fat, muscle, and a fat-muscle intermediate. For each part of the anatomy, the desired Hounsfield units (HU) were found from a patient CT image. The base formula for the deformable anatomy consisted of VytaFlex® 10 and SO-FLEX® (Smooth-on). Brass powder was added to this base to generate the different HU for the different parts of the anatomy. Since the base formula has a higher HU than fat, all parts of the deformable anatomy were targeted to roughly 100 HU higher than that found in the patient CT. Table 1 displays the recipes for all the parts of the anatomy. In Table 1, a "unit" is an arbitrary measure of weight.

TABLE 1

| Anatomy | Recipe | Desired HU | Obtained HU |
|---|---|---|---|
| Bone | Smooth-Cast ® 385, mixed as directed | 2000 | 1888 |
| Fat | 100 units VytaFlex ® 10 part A 100 units VytaFlex ® 10 part B 40 units SO-FLEX ® | 935 | 1041 |
| Muscle | 100 units VytaFlex ® 10 part A 100 units VytaFlex ® 10 part B 40 units SO-FLEX ® 6.1 units brass powder | 1065 | 1158 |
| Fat-Muscle Intermediate | 100 units VytaFlex ® 10 part A 100 units VytaFlex ® 10 part B 40 units SO-FLEX ® 3.05 units brass powder | 1000 | 1103 |

Radiographic Encasement.

Figure 8:
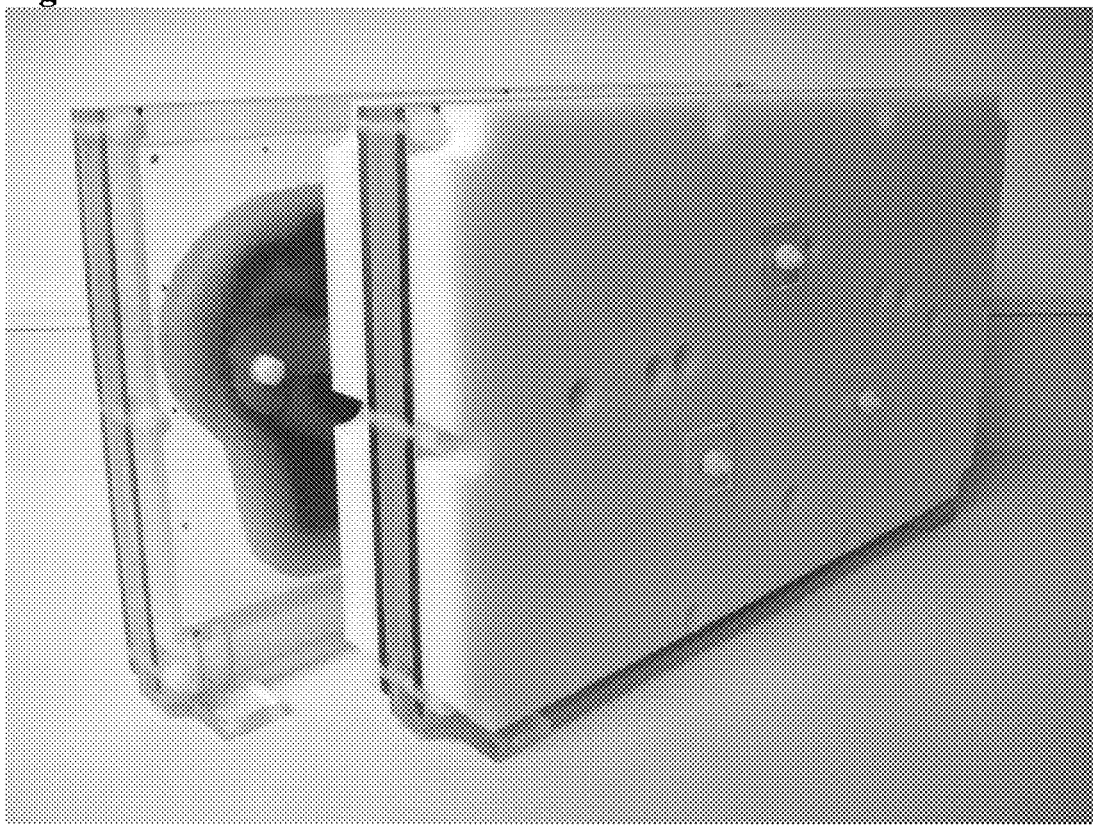
FIG. 8 depicts a radiographic encasement installed about a radiographic phantom as described herein.
Figure 9A:
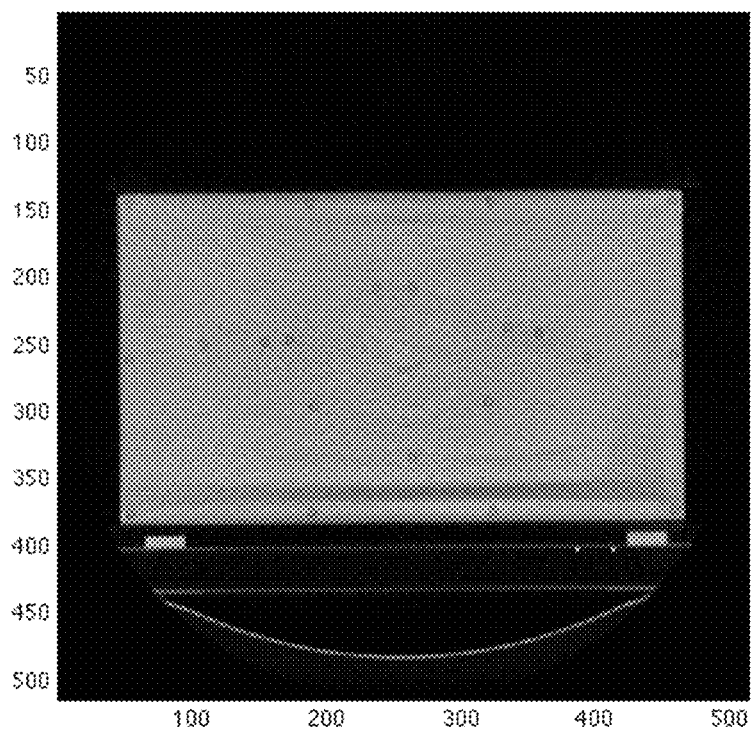
FIGS. 9A-9B.
Figure 9B:
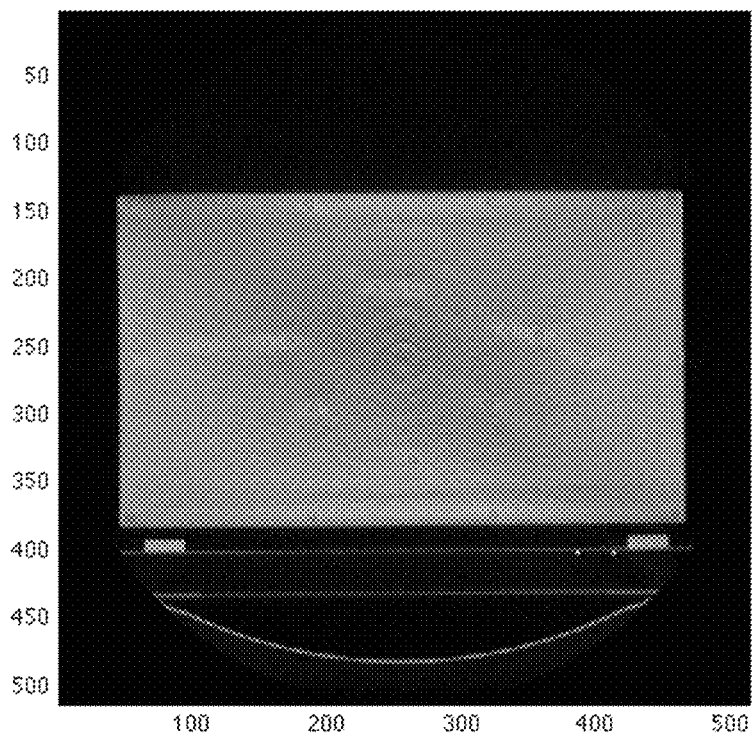

In some embodiments, the radiographic phantom includes an encasement designed to minimize imaging artifacts. If a scan is performed of the phantom without this encasement, imaging artifacts can appear at the abrupt transitions between the phantom acrylic sheets and air. Subjects for CT scans typically do not possess such abrupt transitions. Accordingly, CT machines have not been built to properly scan these transitions. The encasement is a sheet of plastic or other material, e.g., 0.1, 0.2, 0.3, 0.4, 0.5, 0.6, 0.7, 0.8, 0.9, 1.0 inch or even thicker, affixed to the front and back of the phantom and encasing the phantom. FIG. 8 shows a typical radiographic encasement. An exemplary CT scan of a radiographic phantom as described herein is shown in FIG. 9A with the radiographic encasement in place during CT data acquisition. In contrast, FIG. 9B shows a variety of artifacts in the absence of a radiographic encasement under equivalent CT data acquisition conditions.

Optical Markers.

In some embodiments, the radiographic phantom described herein includes optical markers. The markers are painted on using e.g., a mask. To improve the ability to differentiate these markers from the surrounding tissue, in some embodiments a glow-in-the-dark paint is employed that sticks to the deformable material, e.g., urethane rubber. The paint mixture can employ a variety of components, e.g., 5 units (by weight) of Brush-On 40 part B, 4 units of Brush-On 40 part A, 2 units of the G12 Powder, and 8 units of mineral spirit.

Phantom Construction.

An exemplary method for construction of a radiographic phantom pair follows. As shown in FIGS. 10A-10B, the phantom is modeled after a slice of a CT image for a prostate cancer patient. A follow-up CT of the patient was obtained (FIG. 10B), which showed significant difference in deformation from the amount of fluid in the bladder.

Figure 10D:
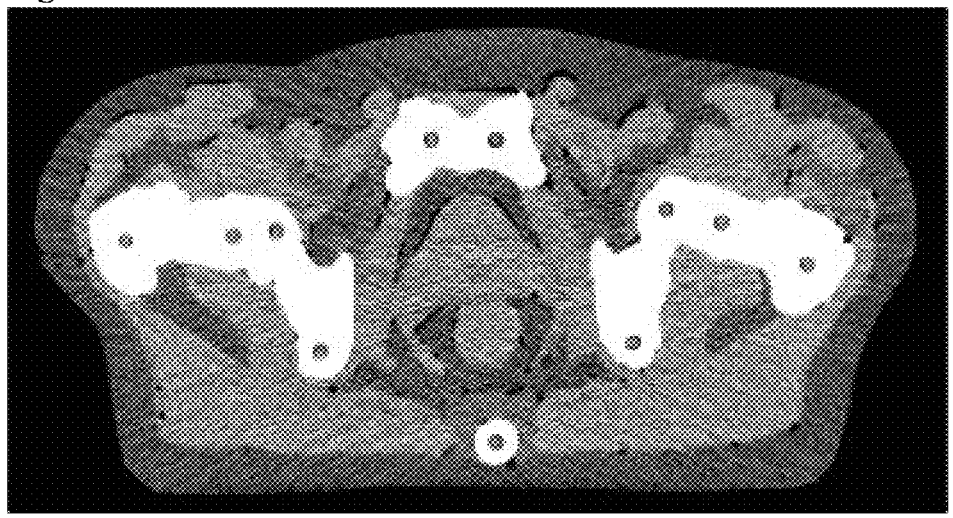
Figure 11A:
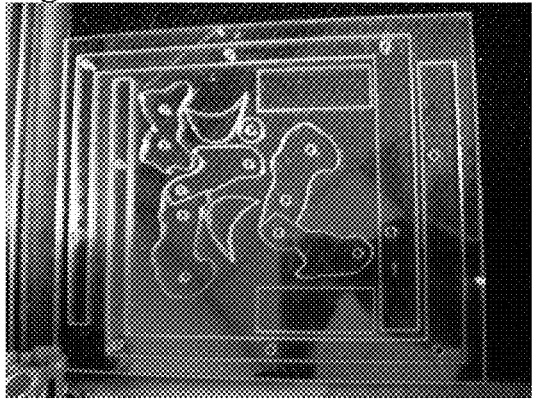
FIGS. 11A-11D.
Figure 11B:
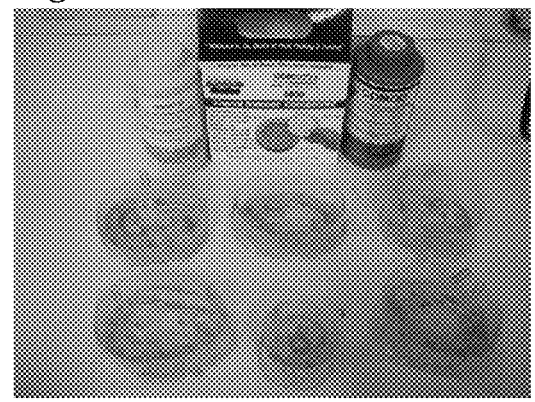
Figure 11C:
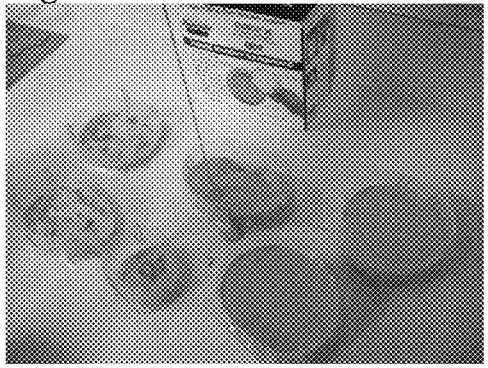
Figure 11D:
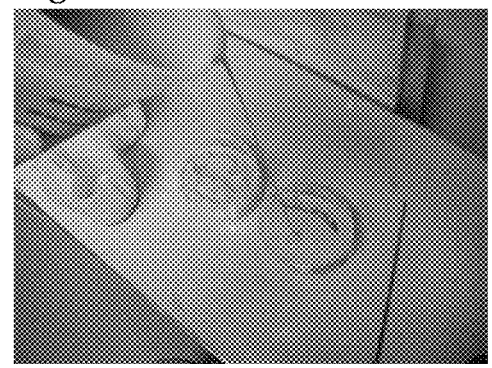
Figure 12A:
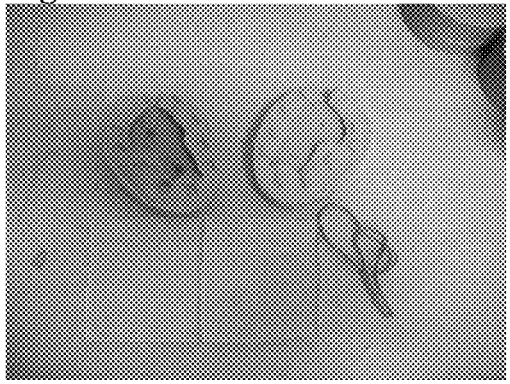
FIGS. 12A-12F depict the sequential steps of casting members of the bony anatomy. See Example 2.
Figure 12B:
Figure 12C:
Figure 12D:
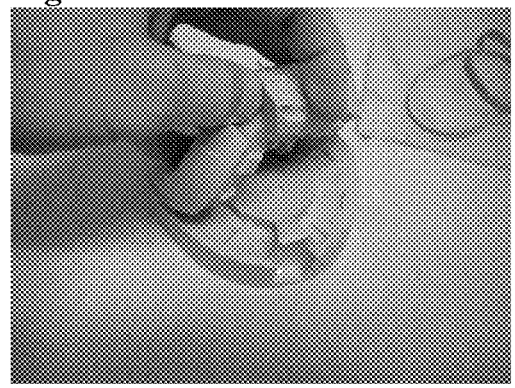
Figure 12E:
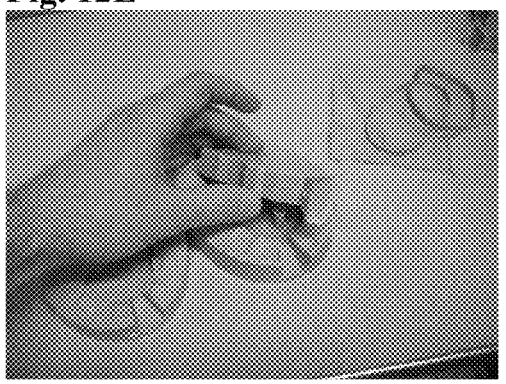
Figure 12F:
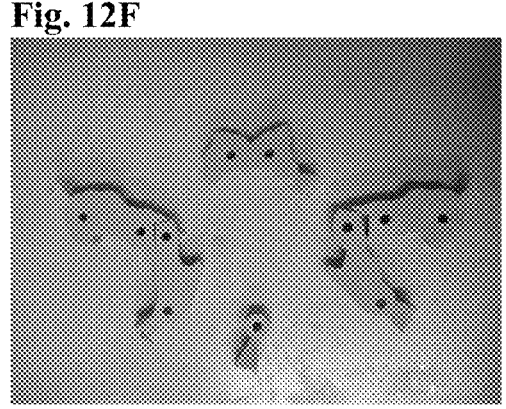

Initially, the area was divided into a set of geometric shapes, shown in FIG. 10C. Then, these shapes are sorted according to their HU into the four categories: bone, fat, muscle, and an intermediate between muscle and fat. These categories are cast in slightly different ways. For comparison to the patient CT image, that of the phantom is also shown in FIG. 10D.

Construction of Bony Anatomy.

A description of a process useful to create the bony anatomy follows. The pieces in this category are first cut out of a sheet of acrylic using a laser cutter (60 Watt Epilog $CO_2$ laser). Then, two-part molds were constructed for them from OOMOO® 25 silicon rubber (Smooth-on, Inc., Easton, Pa.). See FIGS. 11A-11D.

Figure 13A:
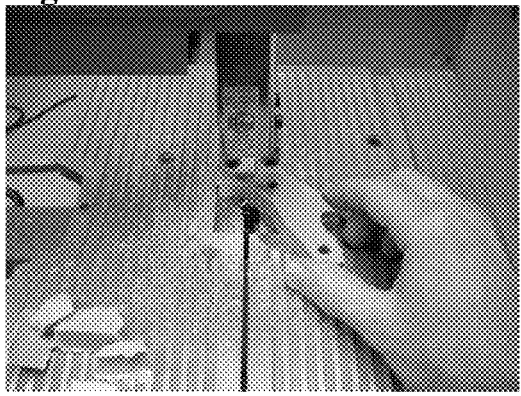
FIGS. 13A-13C. After the casting process of FIGS. 12A-12F (Example 2), the flashing was removed (FIG. 13A) and the parts were prepared (FIG. 13B) for use in the phantom. The final bony anatomy parts are depicted in FIG. 13C.
Figure 13B:
Figure 13C:
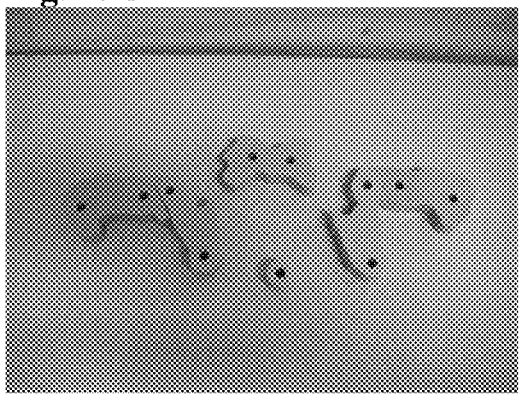
Figure 14A:
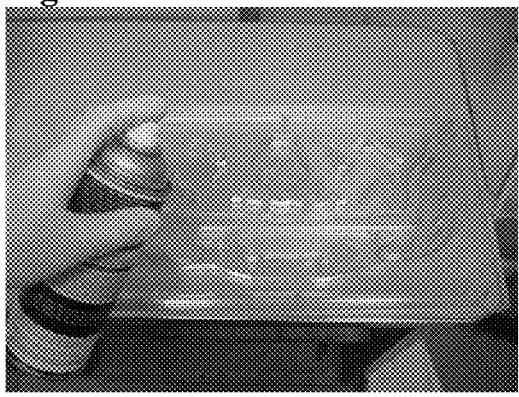
FIGS. 14A-14H depict the sequential steps for production of fatty parts of the anatomy. See Example 2.
Figure 14B:
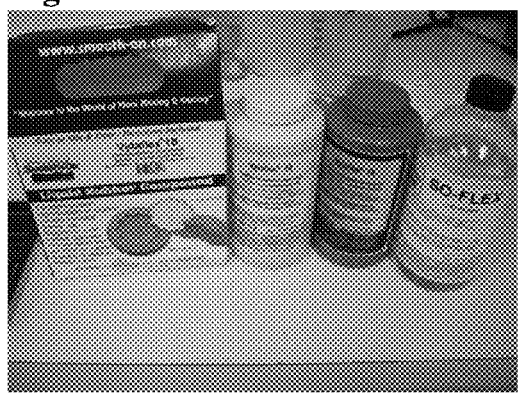
Figure 14C:
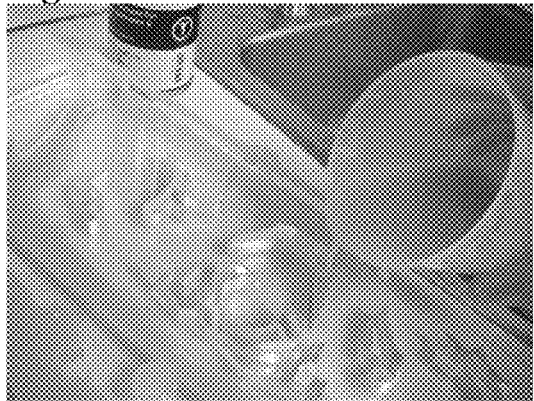
Figure 14D:
Figure 14E:
Figure 14F:
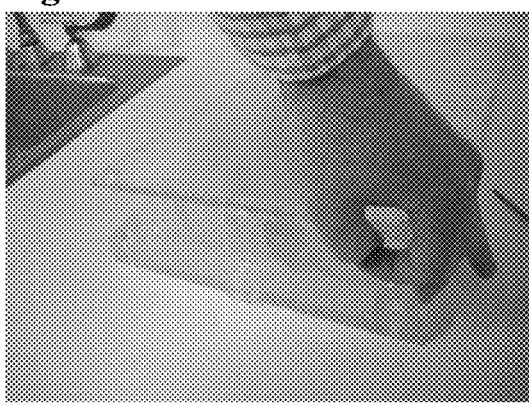
Figure 14G:
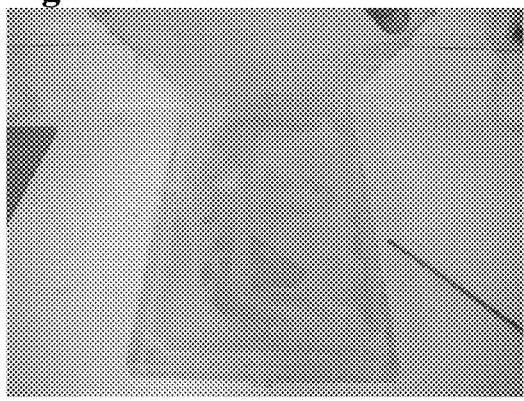
Figure 14H:
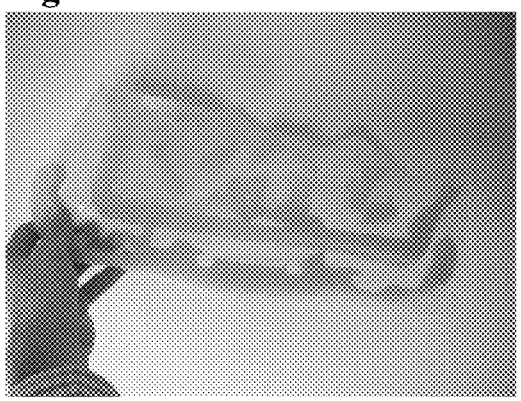
Figure 15A:
FIGS. 15A-15D depict the sequential steps for production of muscle and fat-muscle intermediate parts of the anatomy. See Example 2.
Figure 15B:
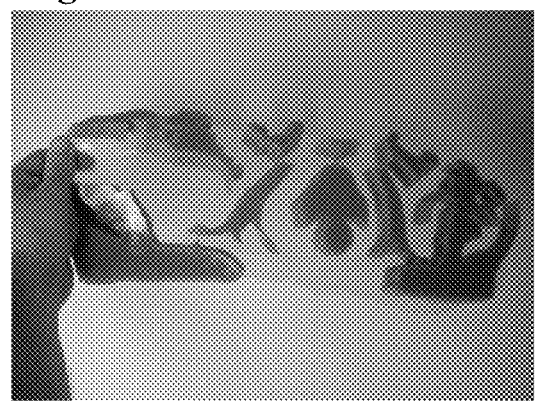
Figure 15C:
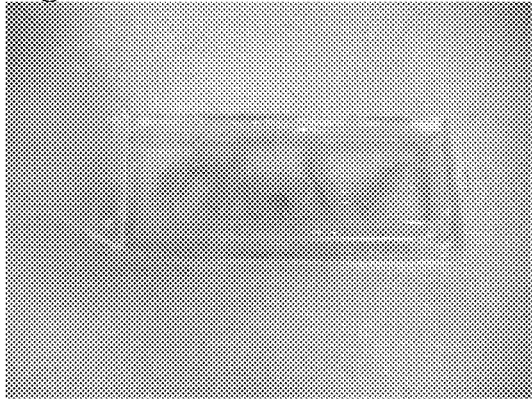
Figure 15D:
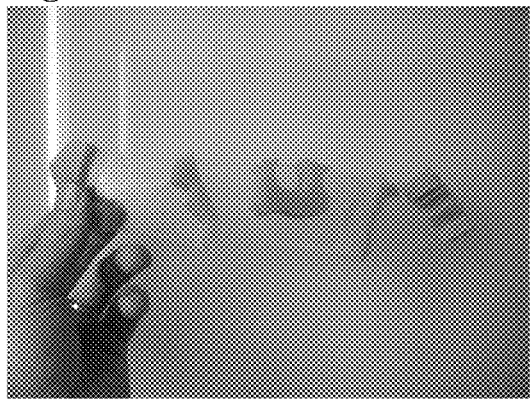
Figure 16A:
FIGS. 16A-16F depict the sequential steps for production of the deformable anatomy. See Example 2.
Figure 16B:
Figure 16C:
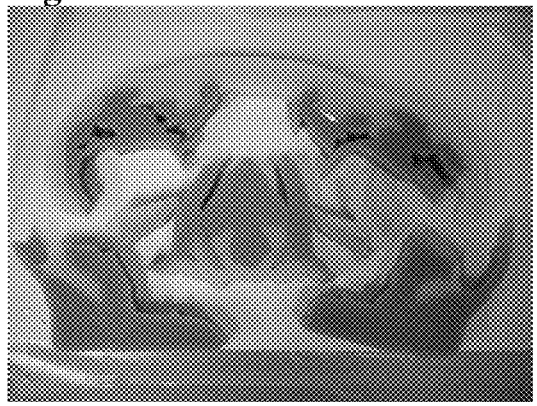
Figure 16D:
Figure 16E:
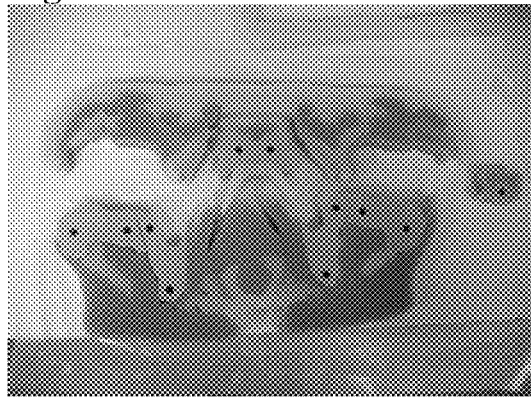
Figure 16F:
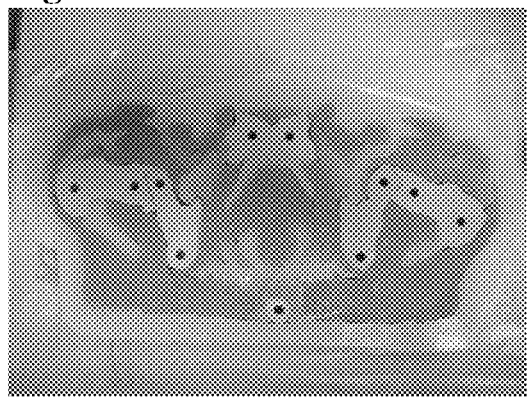

Next, the molds are used to cast the bony anatomy from Smooth-Cast® 385, which is a mineral-filled urethane plastic. This process is shown in FIGS. 12A-12F. Then the flashing was removed, as shown in the sequence of FIGS. 13A-13C.

Construction of Fatty Anatomy.

A description of a process useful to create the fatty part of the anatomy follows. The laser cutter was used to create a mold for this anatomy. This part of the anatomy was cast from a urethane rubber, VytaFlex® 10 (Smooth-on), and a flexibilizer, SO-FLEX® (Smooth-on). The rubber mixture consisted of 100 units (by weight) of VytaFlex® 10 part A, 100 units of VytaFlex® 10 part B, and 40 units of SO-FLEX®. Before pouring the mixture into the mold, a release agent is applied to the mold (Ease Release 200, Smooth-on). This mixture was then poured into the mold and then put into a rotating assembly as it solidified. The use of the rotating assembly facilitated construction of parts of the anatomy that also require a brass powder additive. The rotating assembly method can be used for consistency in construction. Finally, the pieces are de-molded. See FIGS. 14A-14H.

Construction of Muscle and Fat-Muscle.

The muscle and fat-muscle-intermediate parts of the anatomy are constructed in almost the same way as the fatty anatomy. For the muscle, the rubber mixture consisted of 100 units (by weight) of VytaFlex® 10 part A, 100 units of VytaFlex® 10 part B, 40 units of SO-FLEX, and 6 units of brass powder. For the intermediate, the rubber mixture consisted of 100 units (by weight) of VytaFlex® 10 part A, 100 units of VytaFlex® 10 part B, 40 units of SO-FLEX®, and 3 units of brass powder. FIGS. 15A-15D. show the de-molding of these parts of the anatomy.

Assembly of Phantom Material.

The flashing for the deformable anatomy is removed and then the pieces are assembled. Following this, the pieces are glued together using Ure-Bond™ II (Smooth-on). See FIGS. 16A-16F.

Figure 17A:
FIGS. 17A-17B.
Figure 17B:

Next, the phantom covers (i.e., parallel transparent plates) were machined from ¼" thick acrylic plates on a milling machine. An endmill was first used to obtain the correct width and height of these plates. Then, the mounting holes for the deformable slice were drilled. See FIGS. 17A-17B.

In addition to the mounting holes, small depressions can also be drilled into these plates, spaced e.g., 0.5, 1, 2, 3, 4, 5 cm apart or even further. These depressions can be filled with a mixture of brass powder and Smooth-Cast® 385 to create fiducial markers that are visible on a CT scan. An exemplary recipe for this mixture is 43.5 units of Smooth-Cast® 385 part B, 8.7 units of Smooth-Cast® 385 part A, and 2.5 units of brass powder. In some embodiments, the depressions can be filled with a mixture that phosphoresces (i.e., glows in the dark). An exemplary recipe for this mixture is 10 units of Smooth-Cast® 385 part B, 2 units of Smooth-Cast® 385 part A, 2 units of G12 Green Glow powder (Ready Set Glo, Clayton, Wis.), and 1 unit of brass powder.

Optical Markers.

Figure 18A:
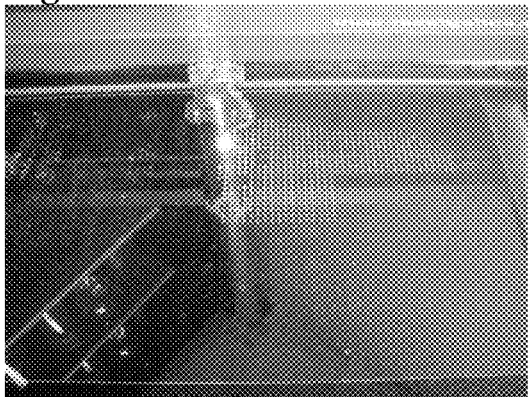
FIGS. 18A-18B depict typical paint masks for the placement of the optical markers.
Figure 18B:
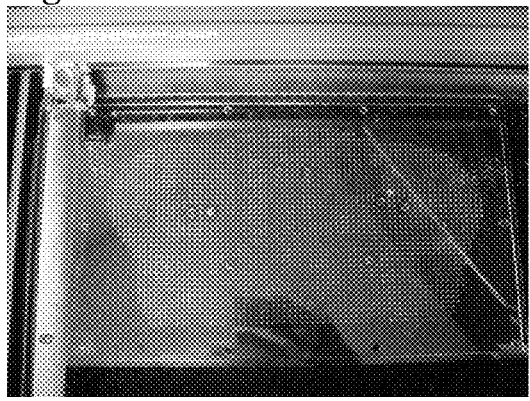
Figure 19A:
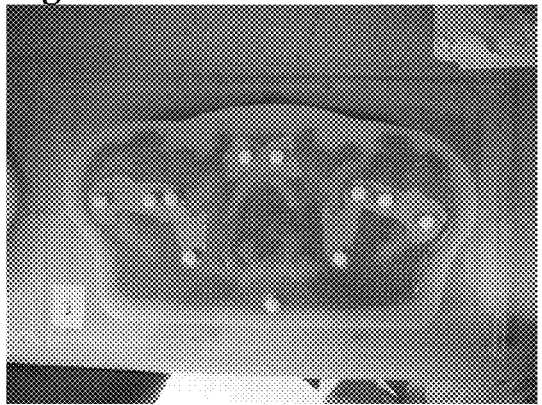
FIGS. 19A-19C depict a phantom slice with paint mask adjacent for painting of the optical markers.
Figure 19B:
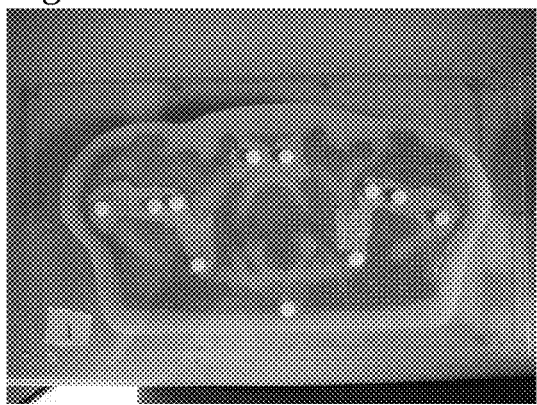
Figure 19C:
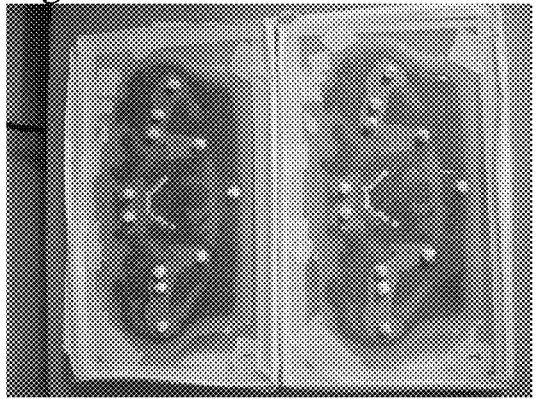

Following the acrylic case assembly, a paint mask for the placement of the optical markers was created from 1/16" thick piece of acrylic on the laser cutter. See FIGS. 18A-18B. The phantom slice was then affixed between this mask and one of the acrylic plates to prepare for painting the optical markers. See FIGS. 19A-19C. Then, glow-in-the-dark urethane paint is made for the optical markers. This paint is made from Brush-On 40 (a urethane rubber casting material from Smooth-on), mineral spirits, and Extreme G12 Green Glow in the Dark Powder (from Ready Set Glo). The paint mixture consists of 5 units (by weight) of Brush-On 40 part B, 4 units of Brush-On 40 part A, 2 units of the G12 Powder, and 8 units of mineral spirit. This mixture is sprayed onto the phantom using, e.g., an airbrush.

Additional Features.

In some embodiments, the radiographic phantom, or each member of a radiographic phantom pair, is rectangular. In some embodiments, the corners of the phantom are rounded, giving a generally elliptical shape. Without wishing to be bound by any theory, it is believed that a generally elliptical shape is useful in eliminating certain artifacts in CT scanning due to the abruptness of the corners found in certain generally rectangular shapes.

Additionally, the process of gluing all the pieces of the anatomy together can differ between the single radiographic phantom system and the corresponding phantom pair system. Accordingly, in some embodiments, different anatomy parts are cast in one mold. Further to this embodiment, the mold resembles the design for the phantom wherein the individual components (e.g., bony material, muscle, fat and the like) are all made out of acrylic pieces. Accordingly, casting a certain component of the anatomy includes removing all the corresponding pieces and pouring in the casting mixture. Then, a cover is placed on the mold which is allowed to solidify, e.g., in a rotating assembly. Following the solidification of that part of the anatomy, the pieces for the next part of the anatomy are removed, and the process is repeated. This creates one solid slice of the anatomy, without the need for glue.

Example 3

Evaluation of Deformation Algorithm Accuracy

Introduction.

There is currently no validated method to provide quality assurance for deformation algorithms used in a clinical setting. In order to answer this and a variety of other needs, we have developed the two-dimensional (2D) anatomical phantom. Previous methods for performing quality assurance for deformable registration exist but have several shortcomings. For example, landmark tracking compares the motion of landmarks that are visible in the computed tomography (CT) images relative to the transformations calculated by a deformation algorithm. The problem with this method, however, is that any prominent landmark will also stand out to the algorithm and yield a skewed view of accuracy.

Although the phantom described herein is literally constructed in three dimensions, it and its deformations are symmetric with respect to the axial direction, making it function as a 2D system. The reduction of the deformable anatomy to a 2D system allows for the use of non-radiopaque markers on the phantom surface to measure deformation. These markers do not appear on CT images so they do not perturb the deformation algorithms, providing an objective way to obtain the a better determination of the deformation.

Methods and Materials:

The 2D phantom is modeled after two CT images of a patient with a full and empty bladder (see e.g., FIG. 7). A total of 2,093 non-radiopaque markers were printed on the initial surface of the phantom, in a 5 mm by 5 mm grid, and are visible through an acrylic plate. Optical camera images were acquired of the phantom with and without the bladder insert. The marker positions are calibrated in the camera images by fiducials in the acrylic plates.

Eleven different deformable registration techniques were applied to calculate the transformation between the full- and empty-bladder phantom CT images. Two of these techniques are from clinical workstations: the deformable registration available in MIMvista™ Software (see e.g., Piper, J., 2007, *Med. Phys.* 34:2353) and the B-spline deformation algorithm from Velocity Medical Solution, as known in the art. The remaining 9 deformation algorithms are implemented in the Deformable Image Registration and Adaptive Radiotherapy Toolbox (DIRART) for MATLAB®. See e.g., Yang, D., et al., 2011, *Medical Physics* 38:67. These deformable registration methods are Lucas-Kanade (Lucas, B. D., & Kanade, T., 1981, in: Proc. Imaging Understanding Workshop (1981), pp. 121-130), the original Horn and Schunck (Horn, B. K. P., & Schunck, B. G., 1981, *Artif. Intell.* 17:185-203), inverse consistency Horn and Schunck (HS), iterative optical flow (Barron, J. L., et al., 1994, *Int. J. Comput. Vis.* 12:43-77), fast iterative optical flow, symmetric force demons (Thirion, J. P., 1998, *Med. Image Anal.* 2:243-260; Rogelj, P., et al., 2006, *Med. Image Anal.* 10:484-493), fast demons (Wang, H., et al., 2005, *Phys. Med. Biol.* 50:2887-2905), fast demons with elastic regularization, and free-form via calculus of variations (COV) (Lu, W. G., et al., 2004, *Phys. Med. Biol.* 49:3067-3087), as known in the art.

Results and Discussion.

Figure 20A:
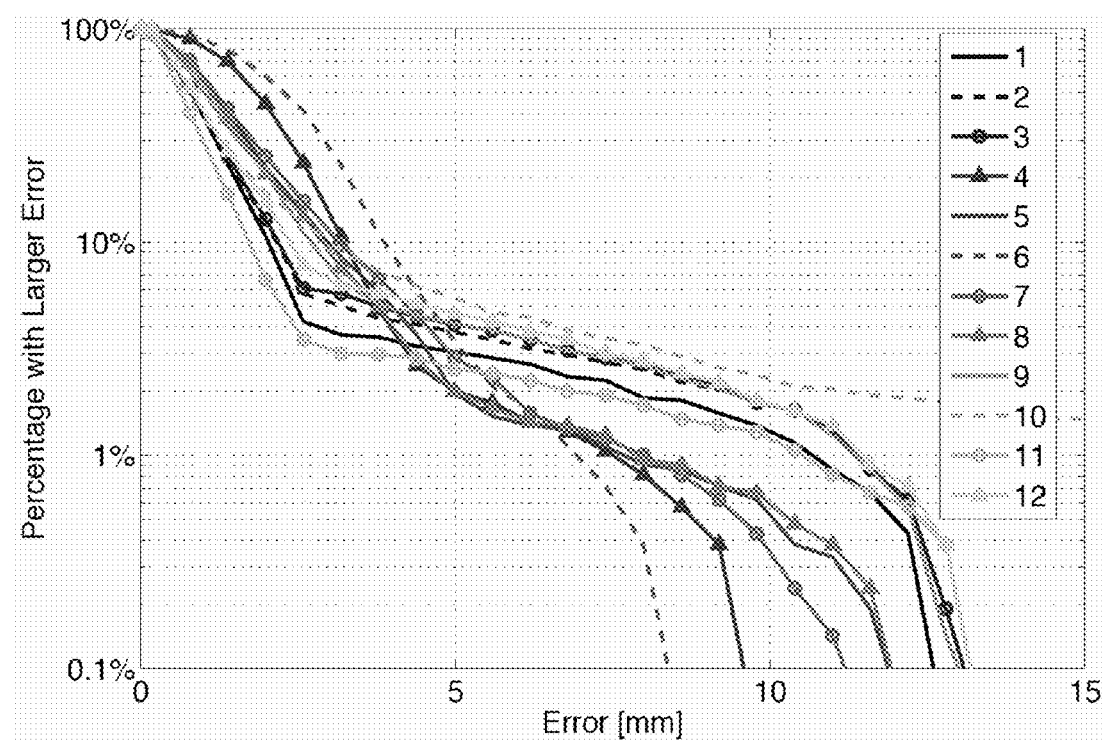
FIGS. 20A-20B.
Figure 20B:
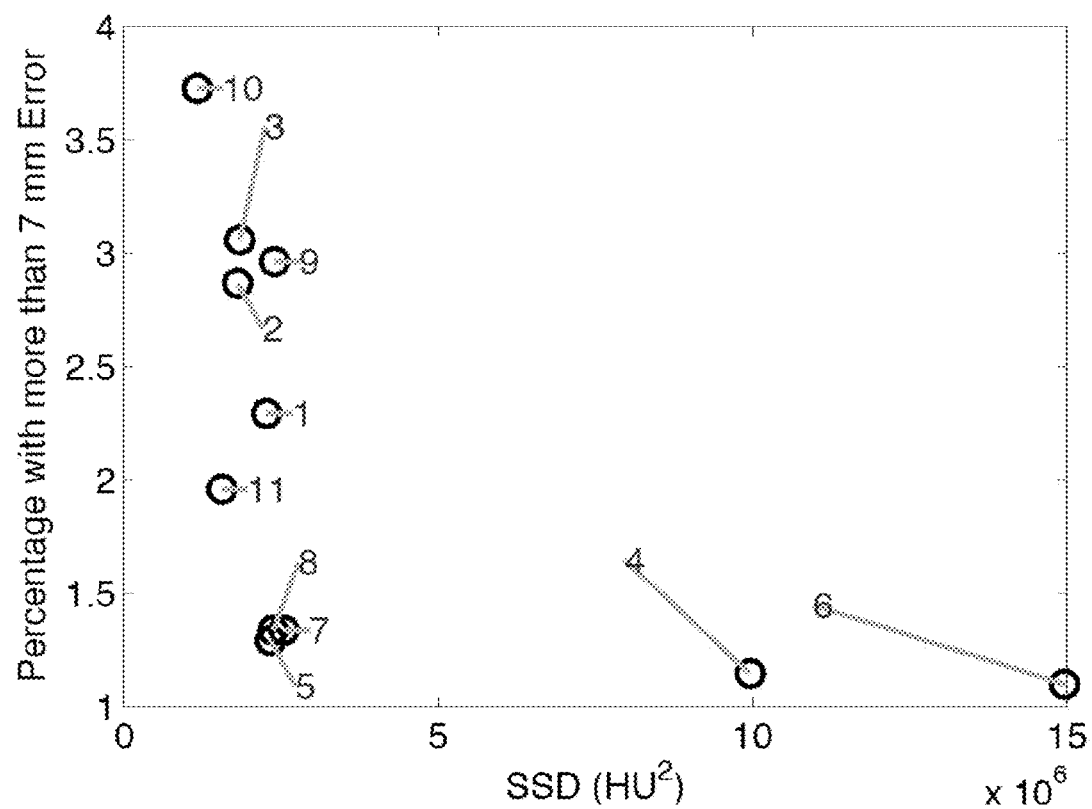

A comparison of the accuracy of the techniques described above are depicted in FIG. 20A. FIG. 20B depicts a plot of algorithm accuracy versus RMS difference as calculated by the SSD statistic over the intensity (square Hounsfield units). The deformation algorithms yield very different results and can be misleading. In fact, MIM, which is clinically implemented, is for the most part less accurate than rigid registration. As is shown in FIG. 20B, MIM achieves the lowest RMS difference, which means it has the highest image similarity. This indicates that, at least for this anatomical site and phantom, MIM focuses too much on image similarity, without enough emphasis on the physical likelihood of a deformation. This demonstrates the need for quality assurance of deformation algorithms.

V. Embodiments

Embodiments of the methods and apparatuses contemplated herein include the following:

Embodiment 1

A method of detecting a difference between a measured optical deformation of a radiographic phantom pair and a theoretical deformation of the radiographic phantom pair, the method including: (i) comparing a first optical image of a non deformed radiographic phantom to a second optical image of a deformed radiographic phantom thereby obtaining a measured optical deformation; (ii) performing a deformable registration method between a first computerized tomography (CT) image of the non deformed radiographic phantom and a second CT image of the deformed radiographic phantom using a deformable registration algorithm thereby obtaining a theoretical deformation; and (iii) comparing the measured optical deformation with the theoretical deformation thereby determining a difference between the measured optical deformation and the theoretical deformation.

Embodiment 2

The method of embodiment 1, further including, prior to step (i), obtaining the first optical image and the second optical image.

Embodiment 3

The method of one of embodiments 1 or 2, further including, prior to step (ii), obtaining the first CT image and the second CT image.

Embodiment 4

The method of one of embodiments 1 to 3, further including, prior to step (i), constructing the non deformed radiographic phantom and the deformed radiographic phantom.

Embodiment 5

The method of one of embodiments 1 to 4, wherein the non-deformed radiographic phantom and the deformed radiographic phantom each include a radiographic phantom material interposed between two parallel plates, the radiographic phantom material including a soft phantom material and a plurality of optically detectable non-radiopaque markers in spatial communication with the soft phantom material

Embodiment 6

The method of embodiment 5, wherein the radiographic phantom material further includes a bony phantom material.

Embodiment 7

The method of one of embodiments 5 or 6, wherein the plurality of optically detectable non-radiopaque markers are fluorescent or phosphorescent

Embodiment 8

The method of one of embodiments 5 to 7, wherein the deformed radiographic phantom further includes a deformation element within the soft phantom material.

Embodiment 9

The method of embodiment 8, wherein the deformation element is a catheter balloon lumen.

Embodiment 10

The method of one of embodiments 1 to 9, further including adjusting the deformable registration method to decrease the difference between the measured optical deformation and the theoretical deformation.

Embodiment 11

The method of embodiment 10, wherein the adjusting includes changing the deformable registration algorithm.

Embodiment 12

The method of embodiment 11, wherein the changing includes evaluating the image similarity of the fixed and warped image in comparison to the statistical noise inherent to the CT images.

Embodiment 13

The method of one of embodiments 11 to 12, wherein the changing includes increasing or decreasing an image similarity value assigned by the deformable registration algorithm based on the evaluation.

Embodiment 14

A radiographic phantom, including: (i) two parallel plates; and (ii) a radiographic phantom material interposed between the parallel plates, wherein the radiographic phantom material includes a soft phantom material and a plurality of optically detectable non-radiopaque markers in spatial communication with the soft phantom material.

Embodiment 15

The radiographic phantom of embodiment 14, wherein the radiographic phantom material further includes a bony phantom material.

Embodiment 16

The radiographic phantom of embodiment 15, wherein at least part of the bony phantom material is rigidly attached to at least one of the two parallel plates.

Embodiment 17

The radiographic phantom of one of embodiments 14 to 16, further including a radiographic encasement substantially enclosing the two parallel plates.

Embodiment 18

The radiographic phantom of one of embodiments 14 to 16, further including a deformation element within the soft phantom material

Embodiment 19

A computerized tomography apparatus including: (i) a CT scanner including an X-ray source and an X-ray detector; and (ii) a radiographic phantom between the X-ray source and the X-ray detector, wherein the radiographic phantom includes (a) two parallel plates; and (b) a radiographic phantom material interposed between the parallel plates, wherein the radiographic phantom material includes a soft phantom material and a plurality of optically detectable non-radiopaque markers in spatial communication with the soft phantom material.

Embodiment 20

The computerized tomography apparatus of embodiment 19, wherein the radiographic phantom material further includes a bony phantom material.

Embodiment 21

The computerized tomography apparatus of embodiment 20, wherein at least part of the bony phantom material is rigidly attached to at least one of the two parallel plates.

Embodiment 22

The computerized tomography apparatus of one of embodiments 19 to 21, further including a radiographic encasement substantially enclosing the two parallel plates.

Embodiment 23

The computerized tomography apparatus of one of embodiments 19 to 22, further including a deformation element within the soft phantom material.

Embodiment 24

A method of detecting a difference between a measured optical deformation of a radiographic phantom pair and a theoretical deformation of the radiographic phantom pair, the method including: (a) receiving a first optical image of a non-deformed radiographic phantom and a second optical image of a deformed radiographic phantom at a system processor; (b) calculating a comparison of the first optical image of the non-deformed radiographic phantom with the second optical image of the deformed radiographic phantom at the system processor, hereby obtaining a measured optical deformation; (c) performing a deformable registration method between a first computerized tomography (CT) image of the non-deformed radiographic phantom and a second CT image of the deformed radiographic phantom using a deformable registration algorithm thereby obtaining a theoretical deformation; and (d) calculating a comparison of the measured optical deformation with the theoretical deformation at the system processor, thereby determining a difference between the measured optical deformation and the theoretical deformation.

What is claimed is:

1. A method of detecting a difference between a measured optical deformation of a radiographic phantom pair and a theoretical deformation of said radiographic phantom pair, said method comprising:
   (i) comparing a first optical image of a non-deformed radiographic phantom to a second optical image of a deformed radiographic phantom thereby obtaining a measured optical deformation;
   (ii) performing a deformable registration method between a first computerized tomography (CT) image of said non-deformed radiographic phantom and a second CT image of said deformed radiographic phantom using a deformable registration algorithm thereby obtaining a theoretical deformation; and
   (iii) comparing said measured optical deformation with said theoretical deformation thereby determining a difference between said measured optical deformation and said theoretical deformation;
   wherein said non-deformed radiographic phantom and said deformed radiographic phantom each comprise a radiographic phantom material, said radiographic phantom material comprising a soft phantom material and a plurality of optically detectable non-radiopaque markers in spatial communication with said soft phantom material, and wherein said deformed radiographic phantom further comprises a deformation element formed of an inflatable catheter balloon disposed within said soft phantom material.

2. The method of claim 1, further comprising, prior to step (i), obtaining said first optical image and said second optical image.

3. The method of claim 1, further comprising, prior to step (ii), obtaining said first CT image and said second CT image.

4. The method of claim 1, further comprising, prior to step (i), constructing said non-deformed radiographic phantom and said deformed radiographic phantom.

5. The method of claim 1, wherein said radiographic phantom material further comprises a bony phantom material.

6. The method of claim 1, wherein said plurality of optically detectable non-radiopaque markers are fluorescent or phosphorescent.

7. The method of claim 1, further comprising adjusting said deformable registration method to decrease said difference between said measured optical deformation and said theoretical deformation.

8. The method of claim 7, wherein said adjusting comprises changing said deformable registration algorithm.

9. The method of claim 8, wherein said changing comprises evaluating the image similarity of the fixed and warped image in comparison to the statistical noise inherent to the CT images.

10. The method of claim 8, wherein said changing comprises increasing or decreasing an image similarity value assigned by said deformable registration algorithm based on said evaluation.

11. A radiographic phantom, comprising:
   (i) two parallel plates;
   (ii) a radiographic phantom material interposed between the parallel plates, wherein said radiographic phantom material comprises a soft phantom material and a plurality of optically detectable non-radiopaque markers in spatial communication with said soft phantom material; and
   (iii) a deformation element formed of an inflatable catheter balloon disposed within said soft phantom material.

12. The radiographic phantom of claim 11, wherein said radiographic phantom material further comprises a bony phantom material.

13. The radiographic phantom of claim 12, wherein at least part of said bony phantom material is rigidly attached to at least one of said two parallel plates.

14. The radiographic phantom of claim 11, further comprising a radiographic encasement substantially enclosing said two parallel plates.

15. A computerized tomography apparatus comprising:
   (i) a CT scanner comprising an X-ray source and an X-ray detector; and
   (ii) a radiographic phantom between said X-ray source and said X-ray detector, wherein said radiographic phantom comprises (a) two parallel plates; (b) a radiographic phantom material interposed between the parallel plates, wherein said radiographic phantom material comprises a soft phantom material and a plurality of optically detectable non-radiopaque markers in spatial communication with said soft phantom material; and (c) a deformation element formed of an inflatable catheter balloon disposed within said soft phantom material.

16. The computerized tomography apparatus of claim 15, wherein said radiographic phantom material further comprises a bony phantom material.

17. The computerized tomography apparatus of claim 16, wherein at least part of said bony phantom material is rigidly attached to at least one of said two parallel plates.

18. The computerized tomography apparatus of claim 15, further comprising a radiographic encasement substantially enclosing said two parallel plates.

19. A method as in claim 1, wherein the radiographic phantom material is interposed between two parallel plates.

* * * * *